US009121606B2

(12) United States Patent
Srinivasachar

(10) Patent No.: US 9,121,606 B2
(45) Date of Patent: Sep. 1, 2015

(54) METHOD OF MANUFACTURING CARBON-RICH PRODUCT AND CO-PRODUCTS

(76) Inventor: Srivats Srinivasachar, Sturbridge, MA (US)

(*) Notice: Subject to any disclaimer, the term of this patent is extended or adjusted under 35 U.S.C. 154(b) by 1087 days.

(21) Appl. No.: 12/730,547

(22) Filed: Mar. 24, 2010

(65) Prior Publication Data
US 2010/0178624 A1 Jul. 15, 2010

Related U.S. Application Data

(63) Continuation-in-part of application No. PCT/US2009/034356, filed on Feb. 18, 2009.

(60) Provisional application No. 61/066,247, filed on Feb. 19, 2008, provisional application No. 61/189,045, filed on Aug. 16, 2008, provisional application No. 61/131,952, filed on Jun. 14, 2008, provisional application No. 61/210,885, filed on Mar. 24, 2009.

(51) Int. Cl.
*C01B 31/08* (2006.01)
*F23K 5/00* (2006.01)
*C01B 31/12* (2006.01)
*C04B 7/36* (2006.01)
(Continued)

(52) U.S. Cl.
CPC ............... *F23K 5/002* (2013.01); *C01B 31/08* (2013.01); *C01B 31/12* (2013.01); *C04B 7/36* (2013.01); *C04B 11/02* (2013.01); *C10L 5/361* (2013.01); *C10L 5/366* (2013.01); *C10L 9/08* (2013.01); *C12M 43/02* (2013.01); *C12M 43/06* (2013.01); *C12P 7/06* (2013.01); *F01K 17/02* (2013.01); *C04B 2290/20* (2013.01); *C10B 49/02* (2013.01); *C10B 53/04* (2013.01); *C10B 53/08* (2013.01); *C10B 57/10* (2013.01); *Y02E 50/17* (2013.01)

(58) Field of Classification Search
CPC ............................. C01B 31/082; C01B 31/10
USPC ............ 431/253; 110/165 R, 65 R, 348, 342, 110/229, 233; 432/58; 502/423, 432, 433, 502/435
See application file for complete search history.

(56) References Cited

U.S. PATENT DOCUMENTS 4,050,885 A 9/1977 Nowick et al.
4,094,626 A 6/1978 Boyhont et al.
(Continued)

OTHER PUBLICATIONS

International Search Report and Written Opinion of International Searching Authority issued in PCT/US2009/034356.

*Primary Examiner* — Stuart Hendrickson
(74) *Attorney, Agent, or Firm* — Brian M. Dingman; Dingman, McInnest & McLane, LLP

(57) ABSTRACT

A method in which a parent hydrocarbon-rich material is processed so as to produce both a carbon-rich solid material that has a higher carbon to hydrogen ratio than that of the parent material and a carbon-deficient combustible gas that has a lower carbon to hydrogen ratio than the parent material. In the process, the material is activated by exposing it to a hot gas stream having elevated levels of one or both of carbon dioxide and water vapor. The combustible gas is combusted to produce heat. At least about 80% of the heat is used in one or more endothermic steps that include drying coal or biomass.

9 Claims, 11 Drawing Sheets

(51) Int. Cl.

| | |
|---|---|
| *C04B 11/02* | (2006.01) |
| *C12P 7/06* | (2006.01) |
| *F01K 17/02* | (2006.01) |
| *C10L 5/36* | (2006.01) |
| *C10L 9/08* | (2006.01) |
| *C12M 1/00* | (2006.01) |
| *C12C 11/06* | (2006.01) |
| *C10B 49/02* | (2006.01) |
| *C10B 53/04* | (2006.01) |
| *C10B 53/08* | (2006.01) |
| *C10B 57/10* | (2006.01) |

(56) References Cited

U.S. PATENT DOCUMENTS

| | | | |
|---|---|---|---|
| 4,615,993 A * | 10/1986 | Schirrmacher et al. | 502/55 |
| 4,899,461 A | 2/1990 | Lehtinen | |
| 5,173,921 A * | 12/1992 | Gaylord et al. | 373/115 |
| 6,911,058 B2 | 6/2005 | Calderon et al. | |
| 7,981,835 B2 * | 7/2011 | Srinivasachar et al. | 502/423 |
| 7,988,754 B1 * | 8/2011 | Rich, Jr. | 48/202 |
| 8,002,033 B2 * | 8/2011 | Calderon et al. | 166/257 |
| 8,100,991 B2 * | 1/2012 | Sasauchi et al. | 48/61 |
| 2007/0254807 A1 | 11/2007 | Bisque et al. | |
| 2008/0020089 A1 | 1/2008 | Pearson | |

* cited by examiner

METHOD OF MANUFACTURING CARBON-RICH PRODUCT AND CO-PRODUCTS

CROSS-REFERENCE TO RELATED APPLICATIONS

This application is a continuation in part of PCT/US09/34356 titled "Method of Manufacturing Carbon-Rich Product and Co-Products" filed on Feb. 18, 2009, which itself claimed priority of the following three provisional patent applications: 61/066,247 filed Feb. 19, 2008; 61/131,952 filed Jun. 14, 2008; 61/189,045 filed Aug. 16, 2008. This application also claims priority of provisional patent application Ser. No. 61/210,885 filed on Mar. 24, 2009. The disclosures of all of these prior applications are incorporated herein by reference.

FIELD OF THE INVENTION

The present invention relates generally to the production of a carbon-rich product (e.g. activated carbon) from a hydrocarbon material such as coal and/or biomass with the generation of excess energy and the generation of a co-product which utilizes the excess energy for its production.

BACKGROUND OF THE INVENTION

Many industrial processes require energy for one or more process steps. A typical energy demand is for material drying or water evaporation. Most industrial processes use natural gas or fuel oil for process heat or steam production. Natural gas and fuel oil are premium fuels whose prices fluctuate significantly and are also high-priced. Solid fuels such as coal are a low-cost alternate that can be used is several cases for the same purpose. However, there are operational challenges with using coal, either via combustion or gasification, because of the increased carbon dioxide emissions relative to natural gas and also because of the ash in the coal that causes operational problems such as deposition and fouling of heat transfer surfaces. A new way of using coal for process heating applications or steam generation is required, which will minimize operational issues while at the same time minimize the increase of the carbon footprint (carbon dioxide emissions).

Additionally, the use of solid fuel for energy generation, while resulting in lower operating costs, requires equipment that is more expensive than when using clean fuels such as natural gas. When using a solid fuel, a higher return on capital investment is required via the simultaneous generation of alternate products that carry a higher economic value than just energy supply.

Several carbon-rich products have economic value and end-use applications. These include but are not limited to the following: activated carbon and activated charcoal for various gas cleaning and liquid processing applications; carbon-rich solids that can be used for soil amendment or as carriers of fertilizing compounds for slow-release into the environment; ultra-high surface area carbons for ultra-capacitors; and porous carbons for gas storage or gas separation. The activated carbon used for such applications is manufactured from hydrocarbon materials like coal or coconut shells.

Manufacturing of these carbon-rich products is typically from a hydrocarbon source such as coal or biomass using the steps of pyrolysis (heating in a non-oxidizing environment) and/or further activation (such as reaction with steam at high temperature to increase porosity or surface area). For example, activated carbon with a surface area of 400 m$^2$/g or greater can be produced from lignite coal via the steps of pyrolysis at 450 to 650° C. and reacting with steam at temperatures between 750 and 1000° C. The production of such carbon-rich solids from parent hydrocarbons results in a hydrogen-rich product gas (a mixture of various compounds, in sum, having an elemental H/C ratio more than that of the parent hydrocarbon) that is typically not fully utilized in the manufacturing of the carbon-rich solid. For example a very large fraction of the hydrogen-rich product gas in activated carbon production is burnt and then quenched to reduce the flue gas to an adequate temperature for the gas cleaning apparatus, cleaned, and then exhausted into the environment. Such operation is not efficient and results in emission of pollutants including carbon dioxide that are excessive.

In existing activated carbon production plants, a hydrocarbon material like coal or biomass is typically processed through the steps of (i) drying, (ii) carbonization, and (iii) steam activation (contacting with steam at temperatures greater than about 800° C. to partially gasify the carbonized material and increase its surface activity). These steps can be performed separately, for example, in separate rotary kilns. They can also be performed in one reactor such as a multiple hearth furnace. Instead of steam, carbon dioxide can also be used in the activation step. Both the carbonization and activation steps generate combustible gases (hydrogen-rich product gas). These gases are exhausted from the activation carbon production furnace into a separate combustion chamber where they are oxidized with air to mainly carbon dioxide and water vapor before being sent to an air pollution control system to remove pollutants such as sulfur dioxide and particulate. Steam for the activation step is typically generated in the combustion chamber with a heat exchanger.

The combustible gases from the carbonization and activation steps typically contain condensable tars, which are the product of coal devolatilization. If there are locations in the process equipment that are colder than the condensation temperature, the condensed tars can cause deposits and fouling of the process equipment. The tars will remain in the gaseous phase if the temperature is maintained above their condensation point, which typically ranges between 300-650° F. For the above reason, the combustible gases from the carbonization and activation steps have to be maintained at relatively high temperatures, pressurized and transported using blowers which consume substantial energy, and combusted in a burner/combustion chamber that needs to be physically closely coupled to the carbonization and activation reactors.

Up to 1 pound of steam per pound of feed coal may be required for the activation furnace or about 1000-1200 Btu per pound of feed. This only represents about one-fifth the energy in the combustible gases. In current generation plants, the remainder of the energy is wasted, resulting in a combustible gas energy utilization of only about 20%. For example, the gases are cooled with a water quench before being directed to an air pollution control system. Greater than about 60 percent of the heat in the original starting material for the production of activated carbon is exhausted into the environment without beneficial use.

Alternatively, in US Patent Application Publication No. 20070254807, an elaborate and expensive steam-to-electricity system is added on to extract some of the energy from the combustible gas into a useful product. The efficiency of conversion to electricity in such plants is only about 25 percent of the energy in the combustible hot gases leaving the activated carbon production process. Also a significant amount of equipment and expense is required to set up the power plant, including steam production heat exchangers (boiler), steam turbines and condensers. A major portion of the heat is exhausted to the environment in the condenser section, where the low pressure steam is contacted with cooling water to condense it before its return to the boiler. The cooling water is then cooled in a cooling tower and heat rejected to the environment before being returned to the condenser. The low energy utilization occurs because only the expansion energy associated with the high temperature, high pressure steam is used in a steam turbine and the latent heat of evaporation associated with the water is rejected to the environment.

Yet another potential use for the combustible gases from the production of activated carbon from coal or biomass is its conversion to liquid fuels or chemicals. However, the composition and purity (cleanliness) requirements for the conversion of the combustible gases from the activated carbon production furnace to fuels and chemicals are very demanding. A narrow range of molecular hydrogen ($H_2$) and carbon monoxide (CO) ratios are required. No diluents, such as nitrogen, can be used, requiring the use of pure oxygen in the generation of the combustible gases. The gases also need to be treated and cleaned to remove many contaminants such as sulfur compounds and ash to prevent poisoning of catalysts in downstream processing equipment before their conversion to liquid fuels or chemicals. The application to convert to liquid fuels or chemicals is therefore very expensive and requires extensive equipment and many processing steps.

SUMMARY OF THE INVENTION

It is an object of this invention to use the low-$CO_2$ producing energy content of the combustible gases from the activated carbon production reactor in a simple and cost-effective manner.

A high efficiency (greater than about 50 percent) and low capital cost solution with effective energy utilization (low carbon dioxide emissions/unit of energy use) is a beneficial means of handling the combustible off-gases from an activated carbon production furnace.

The present invention relates generally to the production of a carbon-rich product (e.g., activated carbon) from a hydrocarbon material such as coal and/or biomass with the generation of excess energy and the generation of a co-product (by physically co-locating the manufacturing of the co-product with the carbon-rich product manufacturing) which utilizes about 50% or more of the excess energy for its production. The products that can be co-produced with the carbon-rich product include, but are not limited to, the following:
  i) Paperboard from wood or recycled paper
  ii) Wallboard from gypsum
  iii) Cement clinker from limestone
  iv) Ethanol from biomass or corn
  v) Electricity and space heating and cooling
  vi) Dried/upgraded coal or biomass from moisture-laden coal/biomass.

The combination of the production of the carbon-rich product (e.g. activated carbon), and the production of co-product(s) via energy consuming processes, such as paperboard, gypsum wallboard, cement clinker, ethanol, space heating or coal and biomass drying, provides significant reduction in $CO_2$ emissions, cost savings through requiring fewer pieces of equipment, reducing material inputs, improving operations and increasing efficiency.

Coal and/or biomass processed for the activated carbon plant produces a carbon-deficient (relative to the parent hydrocarbon) combustible gas, which can advantageously be used for process heat in the manufacturing of the co-product, thereby reducing equipment costs, material inputs, and pollutant and greenhouse gas ($CO_2$) emissions. Activated carbon product resulting from the activated carbon production portion of the inventive process may be used in any activated carbon application including, for example, to reduce heavy metal (e.g. mercury) emissions and/or to control NOx emissions in power plant flue gas, for example, coal-fired power plant flue gas, by contacting the NOx-containing flue gas with activated carbon thereby converting NO to $N_2$.

One embodiment of the invention produces a carbon-rich product, such as activated carbon, from a hydrocarbon material, such as coal or biomass, while simultaneously utilizing the energy content to greater than about 50 percent efficiency of the carbon-deficient gases (a mixture of various compounds, in sum, having an elemental C/H ratio less than that of the parent hydrocarbon) released from the conversion of the hydrocarbon material to a carbon-rich product.

Another embodiment of the invention produces one or more products in addition to the carbon-rich product, these additional products ("co-products") requiring one or more endothermic (energy consuming) steps in their manufacturing process, the energy requirements for which are supplied, at least in part, by the combustion of carbon-deficient gases released from the conversion of the hydrocarbon material to the carbon-rich product. The manufacturing activity of the co-product is physically co-located with manufacturing of the carbon-rich product to use the excess energy of the carbon-deficient combustible gases released from the manufacturing of the carbon-rich product.

Another embodiment of the invention reduces carbon dioxide emissions resulting from the use hydrocarbons, such as coal and biomass, while supplying energy to the endothermic steps in the manufacturing of the co-products.

Another embodiment of the invention minimizes the impact of inorganic constituents (ash) in hydrocarbon fuels, such as coal and biomass, on combustion and heat exchange equipment operation, including ash agglomeration and ash deposition.

Another embodiment of the invention utilizes moisture-rich or carbon dioxide-rich gases released during the manufacturing of the co-products (e.g. in a drying step) as an activating gas in the production of the carbon-rich product from the hydrocarbon material.

Another embodiment of the invention utilizes waste hydrocarbon material generated in the manufacturing of the co-products as a raw material in the reactor for the production of the carbon-rich product.

Another embodiment of the invention utilizes partially processed hydrocarbon material generated in the manufacturing of the co-products as a raw material in the reactor for the production of the carbon-rich product.

Another embodiment of the invention contacts the carbon-deficient gases from the carbonization and activation steps with the "dried" and upgraded coal or biomass or the wet coal/biomass or a combination of the "dried" and wet coal/biomass to condense the tars. The amount of "dried" and or wet coal/biomass relative to the amount of tar is adjusted to maintain a dry flowable product (i.e., tar/coal ratio is kept below a value where the combined material does not becomes sticky) The thermal energy in the carbon-deficient gases can be used advantageously dry a portion of the wet coal/biomass while simultaneously the coal/biomass be a site for tar condensation and solidification.

The invention comprises a method and system for co-producing a product (such as gypsum wallboard, paperboard, ethanol or "dried" and upgraded coal or biomass) in an energy consuming process (such as drying) and a carbon-rich product (such as activated carbon) from a hydrocarbon material such as coal or biomass.

In this method, carbon-rich product, such as activated carbon, is produced by carbonizing a hydrocarbon material to yield a carbonized product and carbonization product gases; activating the carbonized product with steam or carbon dioxide to yield activated carbon and activation product gases; such that the combination of the carbonization product gases and the activation product gases have a lower carbon-to-hydrogen (C/H) ratio compared to the parent hydrocarbon material. These carbon-deficient combustible gases are combusted to generate excess energy for use in the manufacture of co-products, which require this input of energy in one or more steps of their production. The use of the carbon-deficient combustible gas as the energy source minimizes the emission of $CO_2$ into the environment compared to complete conversion and utilization of the coal or biomass, either through direct combustion or through complete gasification followed by combustion of the gasification products. Also, by only partially converting the carbon content of the parent material, and not releasing the included ash and other inorganic constituents in the carbon material to interact with each other, issues related to deposition on heat transfer surfaces and agglomeration are minimized or eliminated during the energy generation step of combustion of these carbon-deficient gases.

The parent hydrocarbon material can be coal, peat, lignite, bituminous coal, sub-bituminous coal, anthracite, petroleum coke, wood, biomass, or other hydrocarbon waste material such as recycled paper. The parent hydrocarbon material to be used in the invention can also have water associated with it, such as waste paper sludge.

In one of the embodiments, the parent hydrocarbon material in this invention for the co-product is preferably a moisture-laden material that would benefit from moisture removal and upgrading to a higher energy density material. Preferred parent hydrocarbon materials are peat, lignite, sub-bituminous coals, wood, biomass, or other hydrocarbon waste material such as recycled paper or waste paper sludge.

The carbonization and activation product gases (comprising predominantly carbon-deficient combustible gases) from the carbon-rich product manufacturing process, which have no useful application for any energy consuming steps in the carbon-rich product manufacturing process, are combusted in a burner (or multiple burners) and the sensible and chemical energy in these gases is converted into thermal energy for use in the various steps of the manufacturing of the co-product. This co-product can be, for example, paperboard, gypsum wallboard, ethanol, cement, electricity or space heating.

For example, the hot combustion gases generated in the above step can be used to contact wet materials for drying or for other processes that require heat (endothermic process). Alternatively, or in addition, the carbon-deficient combustible gases can be directed to a boiler (steam generating unit), where the sensible and chemical energy in the combustible product gases from the activated carbon production is converted by reacting with air (combustion), and the hot gases generated from combustion used to make steam at a temperature and pressure that would be adequate for utilization in the energy consuming steps of co-product manufacturing. Alternatively, or in addition, combustible gases can be directed to a furnace [e.g., heat transfer fluid (oil) heating unit)] where the sensible and chemical energy in the product gases from the activated carbon production is converted to heating a "non-contact heat transfer fluid" that would be adequate for utilization in the energy consuming steps of co-product manufacturing.

In all of the above cases, the flue gas generated from the combustion of activated carbon reactor product gases has a lower $CO_2$ content per unit of heat generated than direct combustion of the feed coal or biomass.

The inventive method and system of the combined production of carbon-rich high surface area product, such as activated carbon, which generates net excess energy, and a co-product, which requires a net energy input in its manufacturing process is described in several preferred embodiments below.

This invention features a method comprising providing a parent hydrocarbon-rich material, processing the parent material so as to produce both a carbon-rich solid material that has a higher carbon to hydrogen ratio that that of the parent material and a carbon-deficient combustible gas that has a lower carbon to hydrogen ration than the parent material, the process comprising activating the material by exposing it to a hot gas stream comprising elevated levels of one or both of carbon dioxide and water vapor, combusting the combustible gas to produce heat, and using at least about 50% of the energy content of the combustible gas in a separate but physically proximate process comprising at least one endothermic step. The carbon-rich solid material may be activated carbon with surface area of at least about 200 $m^2/gm$, and more preferably at least about 400 $m^2/gm$.

The endothermic step may include generating electricity. The electricity may be generated by using the heat to produce steam that is used to drive a turbine. The method may further include using the steam leaving the turbine in a heating or drying step in the separate but physically proximate process, thereby using at least about 70% of the energy content of the combustible gas. The electricity may be generated by a gas engine or other device, and the hot exhaust from such a device is used to generate steam that is used in the separate but physically proximate process.

The endothermic step may be a step of a separate but physically proximate process selected from the group of separate processes including ethanol production, paperboard production, gypsum wallboard production, moisture-laden coal and biomass drying and cement production. The method may further include adding supplemental fuel to the combustible gas before the combusting step, to more closely meet the thermal needs of the separate but physically proximate process. The endothermic step may involve water evaporation or drying, material heating, or calcinations. The method may further include using the heat produced from combustion in a separate process comprising at least one endothermic step, the separate process resulting in part in a gas stream comprising elevated levels of one or both of carbon dioxide and water vapor, and then using the gas stream at least in part as either the hot gas stream for activation of the carbon-rich solid material, or to cool the carbon-rich solid material.

The separate but physically proximate process may include ethanol production. The heat from combustion may be used to generate steam that is used in one or more endothermic steps of the ethanol production. The method may further include adding supplemental fuel to the combustible gas before the combusting step. The ethanol production may result in the emission of volatile organic compounds (VOCs), wherein the at least some of the VOCs are used as a supplemental fuel. The ethanol production may result in the emission of volatile organic compounds (VOCs), wherein the at least some of the VOCs are combusted to produce heat used in the step of processing the parent material so as to produce both a carbon-rich solid material that has a higher carbon to hydrogen ratio that that of the parent material and a carbon-deficient combustible gas that has a lower carbon to hydrogen ratio than the parent material.

In an example of the inventive method, 9580 lb/h of activated carbon is produced from 46,684 lb/h of lignite coal. The carbon-deficient combustible gases generated in the activated carbon production are separately combusted to generate 163, 250 lb/h of steam required for a co-located production of 5820 gallons/h of ethanol. The $CO_2$ emission from the two separate but co-located processes is 35,510 lb/h. The $CO_2$ emissions from the inventive method are significantly lower than the case where the parent hydrocarbon is used as fuel. For the same quantity of steam generation and ethanol production as the above case, 40,700 lb/h of $CO_2$ emissions are generated by using the parent hydrocarbon. Even more remarkably, the individual production of activated carbon (9580 lb/h) and ethanol (5820 gallons/h) would generate a total of 76, 210 lb/h of $CO_2$. The inventive method provides a greater than 50 percent reduction in $CO_2$ emission in the production of valuable products compared to current manufacturing methods.

The separate but physically proximate process may include paperboard production. The heat of combustion may be used to generate hot gas or steam that is used to dry the paperboard. The method may include adding supplemental fuel to the combustible gas before the combusting step, to generate sufficient steam for paperboard production. The parent material may include cellulosic waste from the paperboard production.

The separate but physically proximate process may include gypsum wallboard production. The method may further include adding supplemental fuel to the combustible gas before the combusting step.

The separate but physically proximate process may include cement production. The method may include adding supplemental fuel to the combustible gas before the combusting step.

The separate but physically proximate process may include the drying of additional quantities of parent hydrocarbon material to generate a dry and higher energy density co-product which is the modified hydrocarbon with lower moisture content. The heat from combustion may be used to generate steam that is used in one or more of the drying and heating steps. The method may further include adding supplemental fuel to the combustible gas before the combusting step. The drying of the wet parent hydrocarbon may result in the emission of volatile organic compounds (VOCs), wherein the at least some of the VOCs are used as a supplemental fuel. The drying may result in the emission of volatile organic compounds (VOCs), wherein the at least some of the VOCs are combusted to produce heat used in the step of processing the parent material so as to produce both a carbon-rich solid material that has a higher carbon to hydrogen ratio that that of the parent material and a carbon-deficient combustible gas that has a lower carbon to hydrogen ration than the parent material.

In an example of the inventive method, 1025 kg/h of activated carbon is produced from 5,000 lb/h of lignite coal. The carbon-deficient combustible gases generated in the activated carbon production are separately combusted to generate hot gases used to dry 51,000 kg/h of wet coal to 36,345 kg/h of "dry" coal product. The $CO_2$ emission related to the combustion of the combustible gases is 3,803 kg/h for the production of both the activated carbon and "dry" coal product. This compares to $CO_2$ emission of 3,867 kg/h if the parent hydrocarbon had been used as the fuel for generating the hot gases to dry the moisture-laden coal, which is higher than that for the inventive method. Even more remarkably, the individual production of activated carbon (1,025 kg/h) and "dried" coal (36,345 kg/h) would generate a total of 7,670 kg/h of $CO_2$. The inventive method provides a greater than 50 percent reduction in $CO_2$ emission in the production of valuable products compared to current manufacturing methods.

The invention also features a method comprising providing a parent hydrocarbon-rich material, processing the parent material so as to produce both a carbon-rich solid material that has a higher carbon to hydrogen ratio than that of the parent material and a carbon-deficient combustible gas that has a lower carbon to hydrogen ration than the parent material, the process comprising activating the material by exposing it to a hot gas stream comprising elevated levels of water vapor, combusting the combustible gas to produce heat, using the heat produced from combustion in a separate process comprising at least one endothermic step, the separate process resulting in part in a gas stream comprising elevated levels of water vapor, and using the gas stream at least in part as either the hot gas stream for activation of the carbon-rich solid material, or to cool the carbon-rich solid material. This process preferably utilizes at least about 50% of the energy of the combusted carbon-deficient gas.

BRIEF DESCRIPTION OF THE DRAWINGS

Various other features and advantages of the present invention will become fully appreciated as the invention becomes better understood when considered in conjunction with the accompanying drawings, in which.

DETAILED DESCRIPTION OF EMBODIMENTS OF THE INVENTION

This invention may be accomplished in a method and system for co-producing a product (such as gypsum wallboard, paperboard or ethanol) in an energy consuming process and a carbon-rich product (such as activated carbon) from a hydrocarbon material such as coal or biomass. This is performed by directing the hydrogen-rich combustible gases from the activated carbon production reactor and using its energy content by combusting it and using the released energy to a high efficiency in the energy consuming steps of manufacturing of the co-product.

The preferred embodiments are described below.

I. Activated Carbon and Ethanol Co-Production

Figure 1:
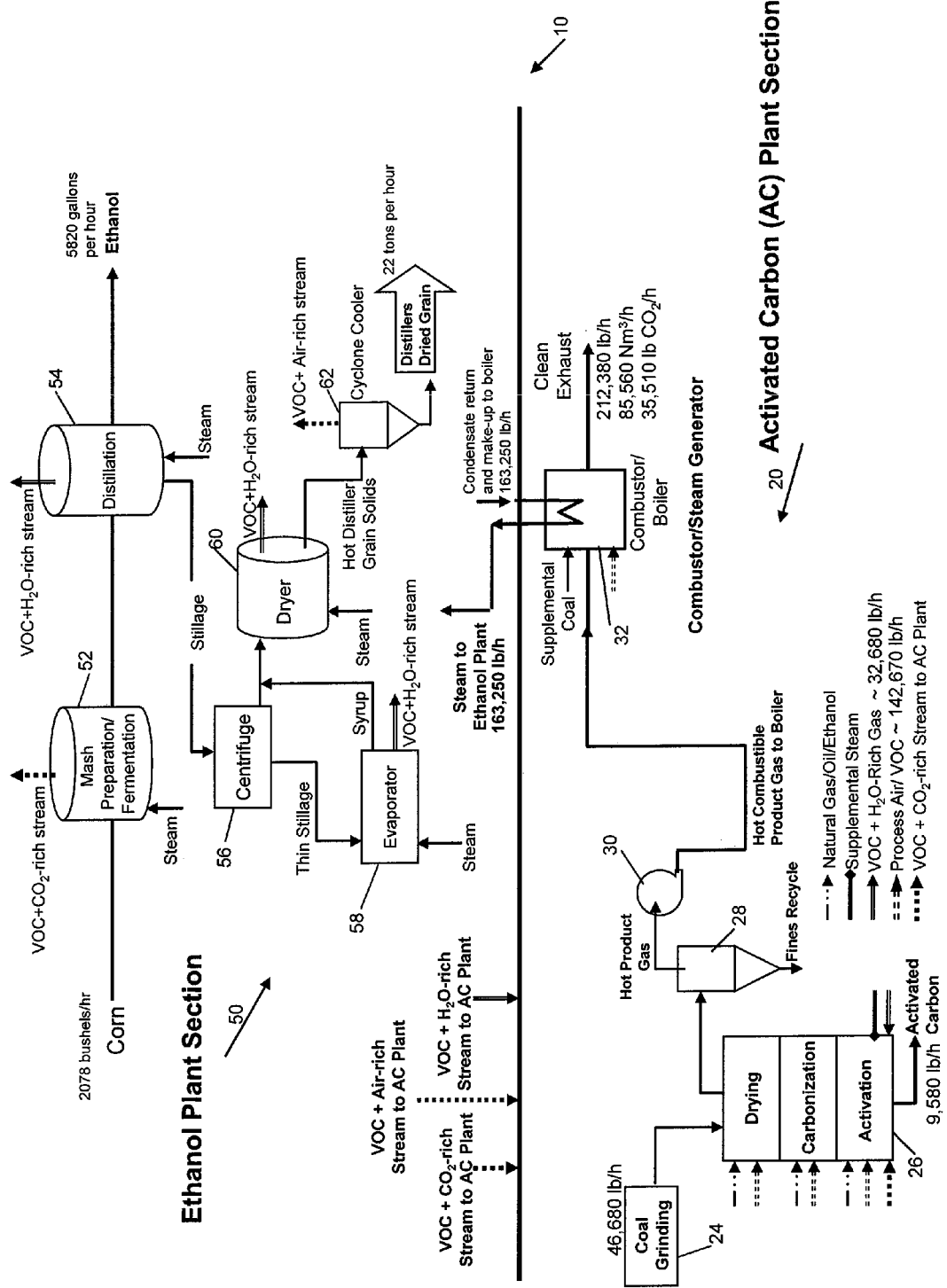
FIG. 1 is a schematic flow diagram of an integrated activated carbon and ethanol production plant according to the invention.

Activated Carbon Production from Hydrocarbon Feedstock and Production of Lower C/H Ratio Hot Combustible Product Gas than Parent Feedstock In this method (FIG. 1) activated carbon and ethanol are produced in co-production plant (10). Activated carbon is produced in the activated carbon manufacturing plant section (20) by carbonizing a solid or partially solid (e.g. wet) carbonaceous material to yield a carbonized product and carbonization product gases; activating the carbonized product with steam or carbon dioxide to yield activated carbon and activation product gases; such that the combination of the carbonization product gases and the activation product gases (hydrogen-rich hot combustible product gases from the activated carbon reactor) have a lower carbon-to-hydrogen (C/H) ratio compared to the parent carbonaceous material. In the above method carbonizing or pyrolysis is typically performed at 400 to 600° C. and activation with steam is performed at 700 to 1000° C.

Activated carbon produced by the above method has a surface area of at least 200 $m^2/gm$, preferably at least, 350 $m^2/gm$, and more preferably at least 500 $m^2/gm$. Surface areas are determined by the Brunauer-Emmett-Teller $N_2$ adsorption method.

A multiple hearth furnace (MHF) may be used as the activated carbon production reactor (26). Coal or other carbonaceous feedstock is prepared via hammer mills (24) to about ⅛" to ½" in size and introduced to the top of the activated carbon production reactor. The carbonaceous material goes through a series of steps including drying, devolatilization and activation in the MHF to product activated carbon. The hot gases leaving the activated carbon production reactor contain fine particulate. The fine particulate, which is partially processed material, is collected in a cyclone (28) and advantageously returned to the reactor for further processing.

Chemical activation of the carbonaceous feedstock instead of physical activation may also be used. In chemical activation, the carbonaceous material is mixed with a dehydrating agent such as zinc chloride, phosphoric acid or alkali hydroxide such as potassium hydroxide. This is followed by heat treatment to temperatures between 450 and 900° C. to carbonize the material and release hot combustible product gases.

In this first embodiment, the co-product manufactured through one or more energy consuming steps is ethanol. In the ethanol manufacturing section (50) of the process (FIG. 1), corn or other high-starch grains (or other biomass used in ethanol production) is first ground into meal and then slurried with water to form a mash. Enzymes are added to the mash to convert the starch to the simple sugar, dextrose. Ammonia is also added for pH control and as a nutrient to the yeast. The mash is processed in a reactor (52) through a high temperature cook step, which reduces bacteria levels prior to fermentation. Steam is used for the high temperature cooking step.

The mash is then cooled and transferred to fermentation vessels where yeast is added and the conversion of sugar to ethanol and carbon dioxide ($CO_2$) begins.

After fermentation, the resulting "beer" is transferred to distillation where the ethanol is separated from the residual "stillage". The ethanol is concentrated to 190 "proof" using conventional distillation in the distillation column (54). Steam is used for the distillation step.

The residual "stillage" from distillation is separated into a coarse grain fraction and a "soluble" fraction by centrifugation in the centrifuge (56). The soluble fraction is concentrated to about 30% solids by evaporation in the evaporator (58). This intermediate is called Condensed Distillers Solubles (CDS) or "syrup." Steam is used for the evaporation process.

The coarse grain and syrup fractions are then mixed and dried to produce distillers dried grain and solubles (DDGS), a high protein animal feed product in the dryer (60). Steam is used for drying step.

As described above, the production of ethanol from corn requires energy, in the form of steam, for various processing steps—about 10% in the cooking process, 30% in the ethanol evaporation, 15% in ethanol distillation and 45% for drying the distiller grains. About 35,000-40,000 Btu of process heat per gallon of ethanol is required. For example, a 50 million pound per year ethanol production plant will use about 1,540 million pounds of steam per year (steam at 365° F., 150 psig). This translates to about 180,000 lbs/hr of steam.

Ethanol may be manufactured by other energy consuming methods such as hydrolysis or gasification and with starting materials such as cellulose. These processes also require energy in their various transformation steps, and this invention covers these methods as well.

Production of Steam for the Ethanol Manufacturing Plant from the Combustion of Hot Combustible Product Gas from the Activated Carbon Production Plant In this embodiment of the inventive process, activated carbon and ethanol are co-produced in a plant (FIG. 1), and at least a portion of the steam (process heat) required for the ethanol section of the plant is produced through the combustion of hydrogen-rich combustible gas generated in the activated carbon production reactor. The combustor/boiler (32) is one known in the art and typically comprises a burner, combustion chamber and heat transfer coils. The heat generated from the combustion process is transferred to water entering the heat transfer coils. Water is converted to a pressurized and hot steam flow that can be advantageously used in the various endothermic steps of ethanol manufacturing.

Cooling of Hot Activated Carbon Product with $CO_2$-Rich or Moisture-Rich Eases from Ethanol Plant Activated carbon leaving the bottom of the activated carbon production reactor, such as a MHF is at a high temperature, typically around 1500 to 1700° F. This hot material is typically cooled with an indirect heat exchanger before being discharged. In an embodiment of the invention, the hot activated carbon product is advantageously cooled with moisture-rich gas stream or $CO_2$-rich gas stream from the ethanol plant in a heat exchanger (not shown). The heat exchanger can be of an indirect contact type, or a direct contact heat exchanger. If direct contact heat exchange is used, the gas streams should have a maximum of about 1 percent $O_2$, preferably less than 0.5% $O_2$ to prevent oxidation and degradation of the activated carbon product. The heat exchanger is preferably operated in a predominantly counter-current mode, with the hot activated carbon product and the "cooling" gas streams flowing in a counter-current fashion. The heated (moisture-rich or $CO_2$-rich) gas stream can then be advantageously used subsequently as process gas in the activation step of the activated carbon plant.

Use of Moisture-Rich or $CO_2$-Rich Exhaust Gases from the Ethanol Manufacturing Plant as Process Feed Gas for Activation in the Activated Carbon Production Reactor In another embodiment of the combined activated carbon and ethanol plant, at least a portion of several exhaust gas streams in the ethanol manufacturing section plant that are almost pure steam (moisture) or $CO_2$ are used as activation process gas. For example, if an indirect steam-driven dryer is used for the production of DDGS, the exhaust gases from the dryer (from the drying process) are almost completely pure water vapor. The gases leaving the fermentation section of the ethanol manufacturing section of the plant are almost completely pure $CO_2$. These streams may be advantageously used as process gas for the activation step in the activated carbon plant. These gas streams may be advantageously preheated as described in the preceding paragraphs before introduction into the activation section of the activated carbon plant. By using the moisture-rich stream from the ethanol plant in the activated carbon plant, water and energy consumption for the combined plant is reduced, since steam required for the activation step in the activated carbon plant does not have be raised separately.

The flue gas from the combustion of the hydrogen-rich combustible gas produced by the activated carbon reactor is treated to reduce the concentration of various pollutants in a manner that is known in the art. For example, ammonia can be injected in the flue gases at a temperature of about 1500-1800° F. to reduce the nitrogen oxides to molecular nitrogen. Alkaline material, such as lime slurry can be injected into the flue gas to capture sulfur oxides, and the coal ash and scrubber particulate can be removed using a dust collector such as a fabric filter.

Co-Firing of Coal and Hot Combustible Product Gas from the Activated Carbon Production Plant for Steam Production for Ethanol Manufacturing In an alternate embodiment, if the ethanol section of the plant requires more energy than what is provided by the combustion of the hydrogen-rich combustible gas from the activated carbon reactor, supplemental firing of additional fuel may be used. This additional fuel can be coal, preferably, or an alternate fuel, such as natural gas.

The hydrogen-rich combustible gas from the activated carbon production reactor may be fired simultaneously with the supplemental fuel in an advantageous manner to reduce pollutant emissions such nitrogen oxides. For example, the hydrogen-rich combustible gas may be preferentially introduced in a reducing zone of the combustor, followed by staged addition of combustion air into the combustor to minimize nitrogen oxide formation and complete combustion. Alternately, the combustible product gas can be introduced into the combustor as a "re-burn" fuel at a downstream location of the combustor to reduce nitrogen oxides formed upstream in the combustor.

Boosting Pressure of the Hot Combustible Product Gas from the Activated Carbon Plant Depending on the operation of the activated carbon reactor, the hydrogen-rich combustible gas from the reactor may need to be delivered at a higher pressure to downstream components/devices than made available at the exit of the reactor. A higher pressure may be required, for example, to obtain better distribution of the combustible gas within a downstream device. In such cases, a fan (30) that can handle hot and particulate-laden gas streams may be used. If the combustible gas from the activated carbon plant has too high a temperature for it to be effectively handled by a fan, then it may be cooled down to the necessary temperature before its introduction into the fan. Cooling may be achieved with a heat exchanger, where additional steam can be generated, or by mixing in a cold gas stream.

Handling of Water/Steam from and to the Boiler/Combustor

The boiler/combustor (32) that burns the combustible gas from the activated carbon reactor has a water inlet and steam outlet. Boiler feed water is compressed to a desired pressure and pumped through the boiler tubes and extracts heat from the hot gases generated from the combustion of the combustible product gas with air. Steam temperature and pressures are chosen to efficiently operate and satisfy the heat demand of the various ethanol manufacturing steps. Typical conditions for steam supply to the ethanol plant are 150 psig pressure and 370° F. temperature.

In some of the production steps in the ethanol plant, steam is contacted directly with other materials. In other production steps such as the drying and production of the DDGS, steam is used in an indirect manner and does not contact other materials. In such cases, the condensed steam (after its useful energy has been transferred) is redirected to the boiler as boiler feed water. Additional (make-up) boiler feed water from a boiler feed water treatment plant is mixed with the returning condensate and then sent to the combustor/boiler.

Destruction of Volatile Organic Compounds in Exhaust Streams from Ethanol Manufacturing in the Activated Carbon Production Plant or the Combustor/Boiler Ethanol manufacturing uses various process steps and pieces of equipment that emit volatile organic compounds (VOC). VOCs may be emitted from the dryer, distillation columns, thermal oxidizer units, wet cake storage locations, fermentation tanks, and other equipment associated with fermentation and distillation such as fluid bed coolers, cooling cyclones (62), and fermentation scrubbers. To prevent emission of VOC into the environment, these streams may be advantageously routed to the combustor/boiler (32). If these streams are oxygen-rich (i.e. predominantly air), they may be advantageously used as combustion air for the combustor/boiler. In this manner, the high temperatures and oxidizing environment in the combustor/boiler can effectively destroy the VOC. To improve heat/process efficiency, these streams may be heat exchanged with the exhaust streams from the combustor/boiler (combustion air pre-heat), prior to being used as combustion air in the combustor/boiler.

The VOC-laden air streams from the ethanol plant can also be used as process air and burner air in the activated carbon production reactor (26), although these quantities are expected to be much smaller than that required for the combustor/boiler.

The fermentation reactor in the ethanol manufacturing plant produces a $CO_2$-rich stream. This stream also has VOCs, which are typically removed with a dedicated scrubber. In this embodiment of the inventive co-production plant, the $CO_2$-rich stream with minor quantities of VOC can be advantageously directed to the activation section of the activated carbon plant and used as activation gas similar to steam. In this manner, a scrubber for the fermentation reactor may be avoided or used only when the activated carbon plant is not operating.

EXAMPLES

Example 1

Ethanol and Activated Carbon Production Plant

An ethanol and activated carbon production plant with the identified improvements (FIG. 1) and advantages relative to stand-alone plants is described below. Coal (lignite) of the composition provided below is used as feed stock.

| | Composition | wt-% |
|---|---|---|
| C | Carbon | 34.6 |
| H | Hydrogen | 3.5 |
| S | Sulfur | 0.61 |
| O | Oxygen | 21.6 |
| N | Nitrogen | 0.66 |
| | Ash | 7.0 |
| $H_2O$ | Moisture | 32.0 |

Activated carbon yield from the activated carbon production reactor is about 20-30 percent based on wet feed input. For a 46,684 lb/hour wet lignite input, this plant yields about 9,580 lb/hour (20% yield) of activated carbon product.

A typical activated carbon composition is shown below obtained from processing the above-described feed stock in the proposed inventive method.

| | Composition | wt-% |
|---|---|---|
| C | Carbon | 68 |
| H | Hydrogen | 0.5 |
| S | Sulfur | 1.5 |
| O | Oxygen | 0.5 |
| N | Nitrogen | 0.7 |
| | Ash | 28.0 |
| $H_2O$ | Moisture | 1.0 |

Steam requirement for activation for the activated carbon production plant is about 0.7 lb of steam per pound of wet feed. For a 46,684 lb/hour wet lignite input, this translates to about 32,680 lb/hour of steam. This quantity of moisture-rich gas is almost completely available from the ethanol DDGS dryer. For example, in the case shown the production amount of DDGS is 22 tons per hour, the corresponding amount of associated moisture would have been approximately 15 tons per hour or 33,000 lbs/hour of water vapor. If additional steam is required, some of the steam generated in the combustor/boiler can be directed to the activation zone of the activated carbon production reactor. In the example discussed here, since the water vapor requirement for the activation step is met almost completely by the dryer exhaust gases of the ethanol plant, no additional fuel firing is required to generate this steam, unlike in a traditional activated carbon production plant.

The carbonization and activation product gases (comprised predominantly of combustible gases) from the activated carbon production reactor are combusted in a boiler (steam generating unit) where the sensible and chemical energy in the activated carbon reactor product gases is converted to making steam at a temperature and pressure that is adequate for utilization in an ethanol plant. The boiler as described above comprises a combustion zone, where activated carbon reactor gases are combusted with air. To completely combust the hot combustible product gas from the activated carbon production reactor, in this example, about 142,670 lb/hour of combustion air is required (corresponding to an excess air of about 20 percent). This air stream is supplied from the various exhaust streams of the ethanol plant, which are predominantly composed of air with trace quantities of VOC. In this manner, a separate VOC destruction device is not required for the ethanol plant.

The steam produced (163,250 lb/hour) in the boiler from the combustion of the hot combustible product gases from the activated carbon reactor is advantageously directed to a corn-to-ethanol plant, where the steam is used as the energy source for various ethanol-manufacturing process steps, including process heat, ethanol distillation, evaporation and concentration of raw stillage, and drying of residual wet solids to dry distillers' grain solids (DDGS).

Alternatively, the steam produced in the boiler from the combustion of the hydrogen-rich combustible gases may also be directed to a power (back pressure) turbine to generate electricity, and exhaust steam from the turbine directed to the corn-to-ethanol plant section for process heat, including, for example, ethanol distillation and evaporation. In this case, the excess energy from the activated carbon production is used for both electricity production and process heat. Electricity may also be produced from the combustible gases directly in a gas engine and the hot exhaust of the gas engine advantageously directed to generate steam for the endothermic steps in the co-product (ethanol) manufacturing.

The flue gas generated from the combustion of activated carbon reactor product gases has a lower $CO_2$ content per unit of heat generated than direct combustion of the feed coal or biomass. For example, in the above example 35,510 lbs/hour of $CO_2$ is generated for the required amount of steam for the ethanol plant operations, compared to 40,700 lbs/hour of $CO_2$ with direct coal combustion in an ethanol plant (see comparative example below).

The energy content in the coal used is about 6400 Btu/lb and the total energy content coming into the process with the coal is 298 MMBtu/hr. The energy content leaving the process with the activated carbon is about 96 MMBtu/hr. The remainder, excluding heat loss to the environment, is about 200 MMBtu/hr and is the energy content of the hydrogen-rich combustible gases. The energy used to evaporate the steam (163,250 lb/hr) is about 170 MMBtu/hr. The efficiency of energy utilization is about 85 percent.

The total amount of coal used for a integrated ethanol and activated carbon plant is 46,684 lb/hour to produce 163,250 lb/hour of steam (required for 5820 gallon per hour ethanol manufacturing plant) and 9580 lb/hour of activated carbon product. In comparison, a separately located coal-fired ethanol plant and a coal-fed activated carbon plant with flue gas quench would require a total of 78,180 lb/hour of coal. The total $CO_2$ emissions from separately located plants would be 76,210 lb of $CO_2$/hour compared to 35,510 lb of $CO_2$/hour for an integrated plant. Even if the separate activated carbon production plant is equipped with recovering the excess heat and converting it to electricity, the efficiency of conversion is only about 20 to 25 percent compared to above about 80 percent for the integrated ethanol-activated carbon plant.

COMPARATIVE EXAMPLES

Example 2

Separate Coal-Fired Boiler for Ethanol Manufacturing

A typical coal-fired boiler necessary for making steam to supply a 50 million pound per year plant (5820 gallons of ethanol per hour) is estimated to be about 163,250 lb/hr of steam. Steam conditions are 150 psig and 365° F. About 32,100 lb/hour of coal firing is required to generate the above steam quantity. The coal considered in this case is a lignite coal as described in the example with the integrated plant. Such a boiler would need to be equipped with heat extraction in the combustion section to keep flue gas temperatures at an operationally acceptable level, if low quantities of excess air (<20 percent) are to be used.

Combustion of the above indicated quantity of coal will generate about 186,380 lb/hour of flue gas, if the excess air used is about 20 percent above the stoichiometric requirement. Corresponding quantity of $CO_2$ emissions in the flue gas is about 40,700 lbs/hour.

Alternatively, if a combustor without heat extraction in the combustion zone is to be employed, flue gas temperatures would need to be moderated typically by cooling with high amounts of excess air (~300 percent). An example of this case would be to use 518,230 lb/hr of air with 36,439 lbs/hour of coal to generate 555,000 lbs/hr of flue gas and 46,197 lbs/hr of $CO_2$ and still only generate the above-identified quantity and quality of steam (163,250 lb/hr, 150 psig and 365° F.)

Example 3

Coal-Fired Activated Carbon Plant with Flue Gas Quench

An example of a typical coal-fired activated carbon production plant is provided below. Lignite of the composition provided in the previous example is used as feed stock. Activated carbon yield is about 20 percent based on wet feed input. A portion of the heat generated from the combustion of the product gases from the reactor is used to generate process steam. Steam requirement for the activated carbon production plant is about 0.7 lb of steam per pound of wet feed. For a 46,684 lb/hour wet lignite input, this translates to about 32,680 lb/hour of steam. This plant yields about 9,580 lb/hour of activated carbon product. The remainder of the heat from the combustion of the product gas from the activated carbon production reactor has to be quenched with a water spray. About 133,380 lb/hour of water is required to quench the flue gases and achieve an outlet flue gas temperature of about 300° F., which is optimum for operation of the pollution control equipment. This process yields an overall flue gas flow of 344,940 lb/hour (20 percent excess air) and $CO_2$ emission of about 35,510 lb/hour, but the energy in the hydrogen-rich combustible gases is not utilized.

Example 4

Coal-Fired Activated Carbon Plant with Heat Recovery for Power Generation

In a typical coal-fired activated carbon production plant flow diagram with heat recovery for power generation, lignite of the composition provided in the previous examples is used as feed stock. Activated carbon yield is about 20 percent based on wet feed input. A portion of the heat generated from the combustion of the product gases from the reactor is used to generate process steam. Steam requirement for the activated carbon production plant is about 0.7 lb of steam per pound of wet feed. For a 46,684 lb/hour wet lignite input, this translates to about 32,680 lb/hour of steam. This plant yields about 9,580 lb/hour of activated carbon product. The remainder of the heat from the combustion of the product gas from the activated carbon production reactor is cooled, while additional steam is generated. This steam is sent to a steam turbine for electricity production. About 10 MWe of electricity can be expected to be produced, with a heat-to-electricity conversion of about 20-25%. This process yields an overall flue gas flow of 212,380 lb/hour (20 percent excess air) and $CO_2$ emission of about 35,510 lb/hour.

Electricity generation using a steam turbine by itself, typically only has energy efficiency utilization between 20 and 35 percent, but for a plant of this size closer to 20 to 25 percent. The remainder of the energy is lost to the environment during steam condensation in the condenser, which is necessary to return water into a liquid state before it can be compressed and returned to the boiler.

II. Activated Carbon and Paperboard Co-production

In another preferred embodiment, (FIG. 2) activated carbon is produced in the activated carbon manufacturing plant section (20) of the activated carbon and paperboard co-production plant (80) from the starting hydrocarbon material such as coal or biomass in a similar fashion as outlined in previous embodiments and the co-product manufactured through one or more energy consuming steps is paperboard. Energy for various endothermic steps of paperboard production is supplied from the excess energy that is generated from activated carbon production and which is associated with the hydrogen-rich combustible gases generated therein.

Figure 2:
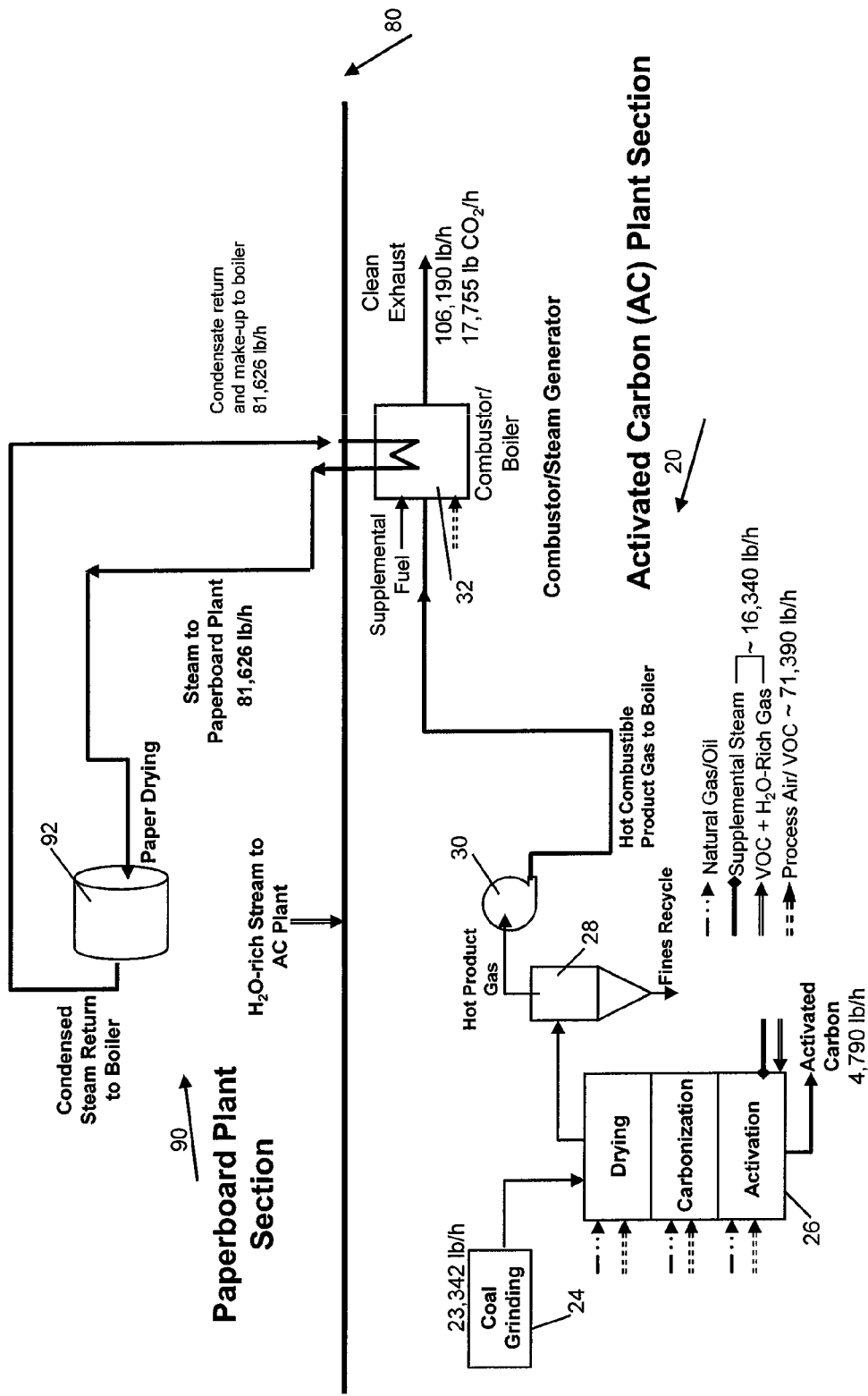
FIG. 2 is a schematic flow diagram of an integrated activated carbon and paperboard production plant according to the invention.
Figure 3:
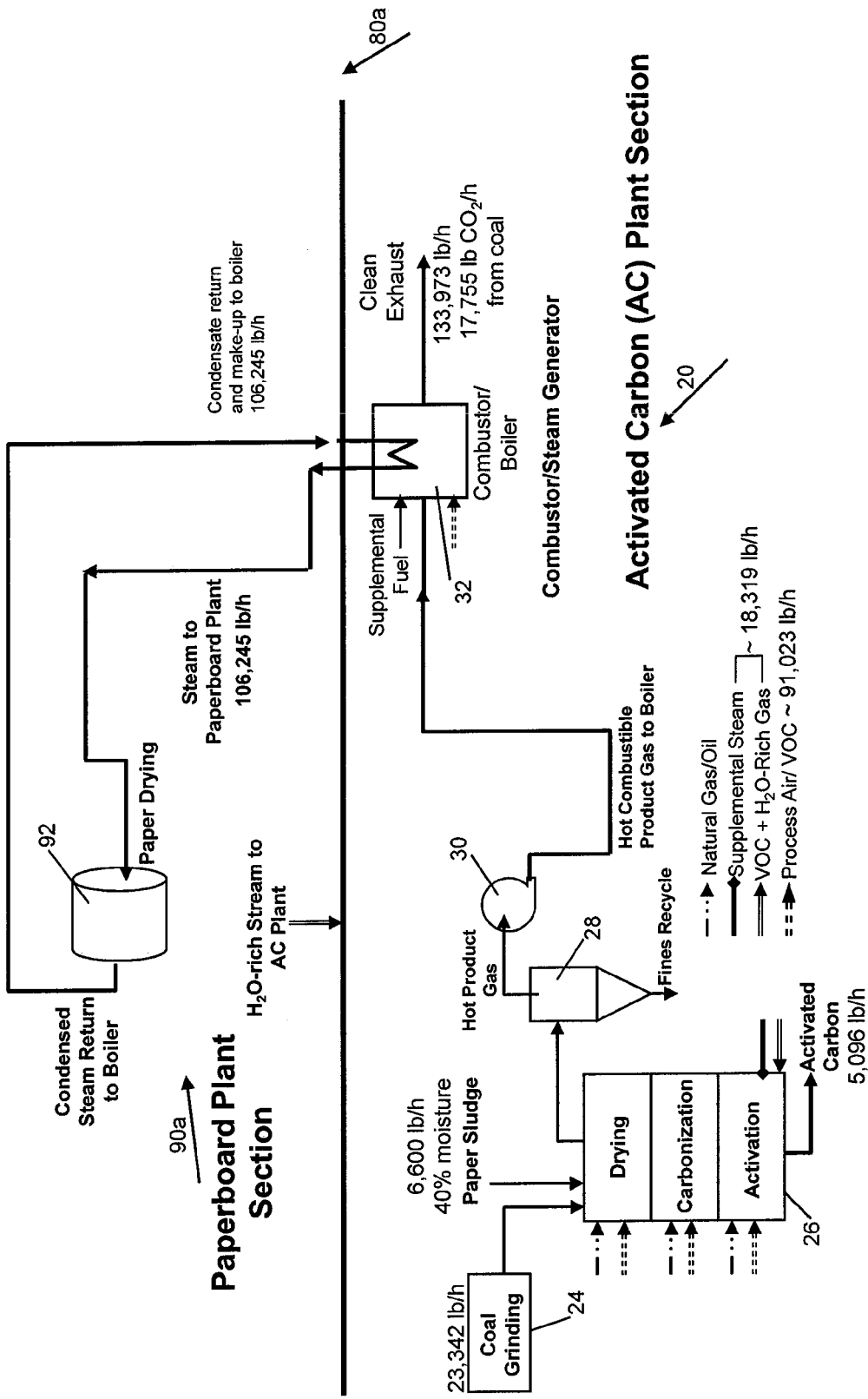
FIG. 3 is a schematic flow diagram of an integrated activated carbon and paperboard production plant with waste paper utilization according to the invention.

FIG. 2 is one embodiment of the present disclosure of a system for an integrated activated carbon and paperboard production process. FIG. 3 is another embodiment of the present disclosure of a system for an integrated activated carbon and paperboard production process with waste paper utilization.

To form paperboard in the paperboard manufacturing section (90), recycled fiber mixed with water and other additives is discharged into a forming line. The "wet" board is then moved to dryer lines (92) where excess moisture is evaporated in a controlled manner. Energy for board drying is supplied by steam. Typically, a drum or a surface heated with steam is contacted with the wet paper for the drying operation. Alternately, an air stream may be heated by the steam via a heat exchanger and the heated air stream supplied to the dryer to evaporate the water.

Typically energy requirement for paperboard production is about 4-8 MMBtu/ton.

Production of Process Heat for Paperboard Manufacturing Plant from the Combustion of Hot Combustible Product Gas from the Activated Carbon Production Plant In this embodiment, hot combustible gases generated from the pyrolysis and steam gasification of the solid or partially solid carbonaceous material such as coal, carbonaceous waste from the paperboard plant, or other biomass is combusted with air in a boiler (32) to generate at least some portion of the process heat/steam for the paperboard manufacturing section of the plant. By using a potentially wasted fuel, the energy costs for the paperboard manufacturing are minimized and efficiency maximized.

In the paperboard making process, a significant amount of wet cellulosic waste is generated during the initial screening process.

Utilization of Carbonaceous Residues/Waste from the Paperboard Plant in the Activated Carbon Production Plant to Produce Activated Carbon and Process Heat/Process Steam In this embodiment (FIG. 3), the carbonaceous residues/waste from the paperboard making steps can be advantageously fed to the activated carbon manufacturing section (20a) at the top of the activated carbon multiple hearth furnace (front of the activated carbon manufacturing process) along side other carbonaceous feed materials to produce activated carbon and hot combustible product gases. Separate or dedicated equipment is not required for processing the residue/waste stream. Since the carbonaceous materials from the paperboard plant are renewable (biomass-derived), the combustible gases generated from the pyrolysis and activation of the said material, their combustion and subsequent heat extraction and utilization will result in less carbon dioxide emissions resulting from the combustion of fossil-derived fuels. The paperboard is co-produced in the paperboard manufacturing section of the plant (90a).

The emissions of pollutants including carbon dioxide can be significantly reduced with the above invention because of the utilization of the waste energy from the carbon manufacturing section of the plant in paperboard manufacturing as well the use of waste carbonaceous ("renewable") materials in the paperboard section of the plant in the activated carbon manufacturing.

Co-Firing of Natural Gas and Hot Combustible Product Gas from the Activated Carbon Production Plant for Process Heat for Paperboard Manufacturing In an alternate embodiment, if the paperboard plant has larger heat requirements than what can be provided by the hydrogen-rich gas from the activated carbon reactor, then supplemental fuel, such as natural gas, may be advantageously co-fired or fired separately in the boiler.

Controlling Temperature of the Gases for Process Heat for Paperboard Manufacturing The temperature required for the drying and other operations may be limited by process considerations. Temperature of the hot product gases generated from the combustion of the hydrogen-rich combustible gases from the activated carbon reactor may be controlled by mixing "cold" recycled flue gas in a proportion to achieve the desired temperature values.

Process Control for Paperboard Manufacturing

In another embodiment, natural gas is used in combination with the combustible product gases from the activated carbon production reactor to enable control of the steam generated for paperboard production. The proportion of natural gas can be minimized and set at values just necessary for process control. Control of the quantity of steam as defined by the requirements of the paperboard plant, is achieved by monitoring the steam quantities generated from the combustible gases from the activated carbon production reactor and supplementing it with natural gas or oil firing. Process control is achieved by varying the amount of natural gas or oil firing and steam generation associated with that firing.

Co-firing of natural gas and activated combustible product gas from the activated carbon production reactor also enables "assured" process operation or back-up fuel in case natural gas supply is interrupted or the activated carbon production reactor has to be shut down.

Similar to the previous embodiment in the co-production of activated carbon and ethanol, the following advantageous aspects are included in the preferred embodiments of co-production of activated carbon and paperboard.

(i) Cooling of hot activated carbon product with moisture-rich gases from paperboard manufacturing.

(ii) Use of moisture-rich exhaust gases from the paperboard manufacturing as process feed gas for carbon activation in the activated carbon production reactor

EXAMPLES

Example 5

Integrated Paperboard and Activated Carbon Production Plant

An integrated paperboard and activated carbon production plant with the identified improvements (FIG. 2) and advantages relative to stand-alone plants is described below. Lignite of the composition provided below is used as feed stock.

| Composition | | wt-% |
|---|---|---|
| C | Carbon | 34.6 |
| H | Hydrogen | 3.5 |
| S | Sulfur | 0.61 |
| O | Oxygen | 21.6 |
| N | Nitrogen | 0.66 |
| | Ash | 7.0 |
| $H_2O$ | Moisture | 32.0 |

The production of process heat for the paperboard production process is described below. About 23,340 lb/hour of coal is introduced into a multiple hearth furnace. About 71,400 lb/hour air and 16,340 lb/hour steam is introduced in the various hearths of the MHF and hot product gas combustor to generate the heat required and provide the optimum gaseous environment for the production of activated carbon as well as combust all hydrocarbon and other combustible gases from the activated carbon production reactor. About 4,790 lb/hour of activated carbon is produced from this reactor set-up. The hot combustible product gases leaving the multiple hearth furnace (activated carbon production reactor—ACPR) at the top is sent to a combustor/steam boiler. Air is added to the burner to completely combust the hydrocarbons to yield hot flue gas, which transfers its heat via a heat exchanger to make product steam (81,630 lb/hour, 370° F.). This steam is sent to the paperboard plant and used for paper drying and other process heating purposes. In the paperboard plant, the steam is condensed, transferring its heat mostly completely to the paper-making process. The loss of heat to the environment is mainly through equipment walls and in the flue gas (clean exhaust) leaving the system.

Overall heat utilization efficiency of greater than 70 percent and more preferably 80 percent of the chemical and sensible heat in the hot combustible product gas from the activation carbon production reactor to boiler is achieved. The condensate obtained from steam condensation in the paper-making process is returned to the boiler to be heated and evaporated again.

In the above set-up, about 17,760 lb of $CO_2$ is generated from coal and 81,630 lb. of steam (at 370° F.) is generated via heat extraction resulting in 0.218 lb $CO_2$ per pound of steam generated. $CO_2$ emission for each pound of steam generated by this method where activated carbon is produced and the remainder (consisting of hydrogen-rich combustible gases) is used for steam production (or heat utilization) is about 12.5 percent lower than the comparative example of direct combustion of coal or combustion followed by complete gasification of coal, where all of the carbon content in the fuel is used for heating.

The energy content in the coal used is about 6400 Btu/lb and the total energy content coming into the process with the coal is 150 MMBtu/hr. The energy content leaving the process with the activated carbon is about 49 MMBtu/hr. The remainder, excluding heat loss to the environment, is about 100 MMBtu/hr and is the energy content of the hydrogen-rich combustible gases. The energy used to evaporate the steam (81,630 lb/hr) is about 85 MMBtu/hr. The efficiency of energy utilization is 85 percent.

Example 6

Integrated Paperboard and Activated Carbon Production Plant with Waste Paper Utilization An integrated paperboard and activated carbon production plant with the identified improvements with waste paper utilization (FIG. 3) and advantages relative to stand-alone plants is described below.

Waste paperboard of the composition provided below is used as feed stock.

| | Composition | wt-% |
|---|---|---|
| C | Carbon | 26.0 |
| H | Hydrogen | 3.5 |
| O | Oxygen | 26.4 |
| | Ash | 4.0 |
| $H_2O$ | Moisture | 40.0 |

Lignite of the composition provided below is also used as feed stock.

| | Composition | wt-% |
|---|---|---|
| C | Carbon | 34.6 |
| H | Hydrogen | 3.5 |
| S | Sulfur | 0.61 |
| O | Oxygen | 21.6 |
| N | Nitrogen | 0.66 |
| | Ash | 7.0 |
| $H_2O$ | Moisture | 32.0 |

The production of process heat for the paperboard production process and utilization of the waste paper sludge in the activated carbon production process is described below. About 23,340 lb/hour of coal is introduced into a multiple hearth furnace. About 6,600 lb/hour of waste paper sludge (40% moisture) is also introduced to the top of the multiple hearth furnace. About 91,000 lb/hour air and 18,320 lb/hour steam are introduced in the various hearths of the MHF and hot product gas combustor to generate the heat required and provide the optimum gaseous environment for the production of activated carbon as well as combust all hydrocarbon and other combustible gases from the activated carbon production reactor. About 5,100 lb/hour of activated carbon is produced from this reactor set-up. The yield of activated carbon based on the feed coal is approximately 20 percent. The yield of activated carbon based on the feed paper waste is approximately 5 percent. The hot combustible product gases leaving the multiple hearth furnace (activated carbon production reactor) at the top is sent to a combustor/steam boiler. Air is added to the burner to completely combust the hydrocarbons to yield hot flue gas, which transfers its heat via a heat exchanger to make product steam (106,250 lb/hour at 375° F.). This steam is sent to the paperboard plant and used for paper drying and other process heating purposes. In the paperboard plant, the steam is condensed transferring its heat almost completely to the paper-making process. The condensate is returned to the boiler to be heated and evaporated again.

In the above set-up, about 17,760 lb of $CO_2$ is generated from coal (no increase compared to Example 5, since a renewable source, i.e. waste paperboard, is used) and 106,250 lb of steam are generated resulting in 0.167 lb $CO_2$ from coal per pound of steam generated. $CO_2$ emission for each pound of steam generated by this method where a renewable source such as waste paper is used for a portion of the feed, activated carbon is produced, and the remainder (consisting of hydrogen-rich combustible gases) is used for steam production (or heat utilization) is about 33 percent lower than the comparative example of direct combustion of coal or combustion followed by complete gasification of coal, where all of the carbon content of the fuel is used for heating.

The energy content in the coal used is about 6400 Btu/lb and the total energy content coming into the process with the coal is 150 MMBtu/hr. The energy content of the waste paper is about 37 MMBtu/hr. The energy content leaving the process with the activated carbon is about 52 MMBtu/hr. The remainder, excluding heat loss to the environment, is about 135 MMBtu/hr and is the energy content of the hydrogen-rich combustible gases. The energy used to evaporate the steam (106,245 lb/hr) is about 110 MMBtu/hr. The efficiency of energy utilization is about 82 percent.

III. Activated Carbon and Wallboard Co-Production

In another preferred embodiment, (FIG. 4) activated carbon and wallboard are co-produced in a plant (100). Activated carbon is produced from the starting hydrocarbon material such as coal or biomass in a similar fashion as outlined in previous embodiments and the co-product manufactured through one or more energy consuming steps is gypsum wallboard. Energy for various endothermic steps of wallboard production is supplied from the excess energy that is generated from activated carbon production and which is associated with the hydrogen-rich combustible gases generated therein.

Figure 4:
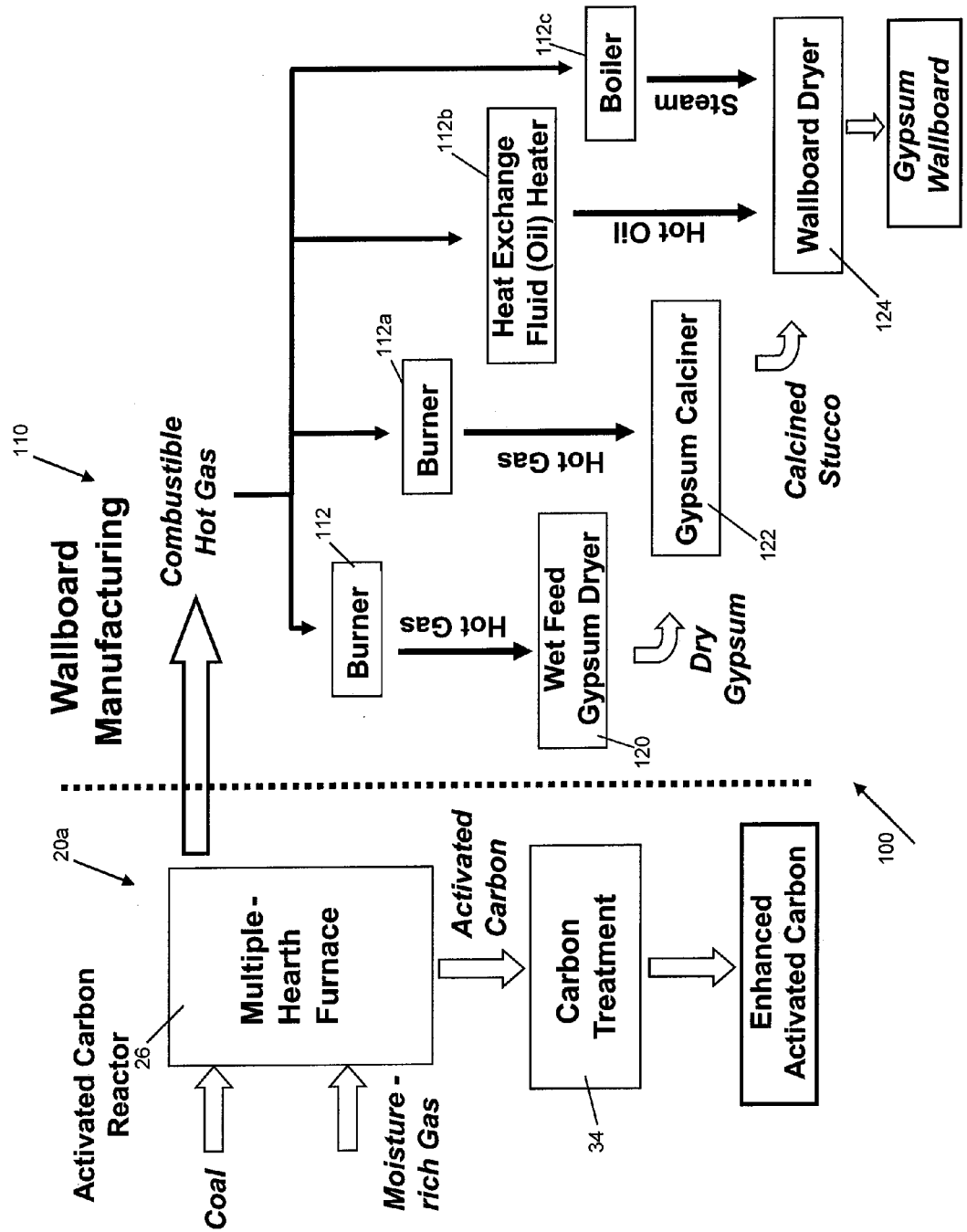
FIG. 4 is a schematic flow diagram of an integrated activated carbon and gypsum wallboard production plant according to the invention.
Figure 5:
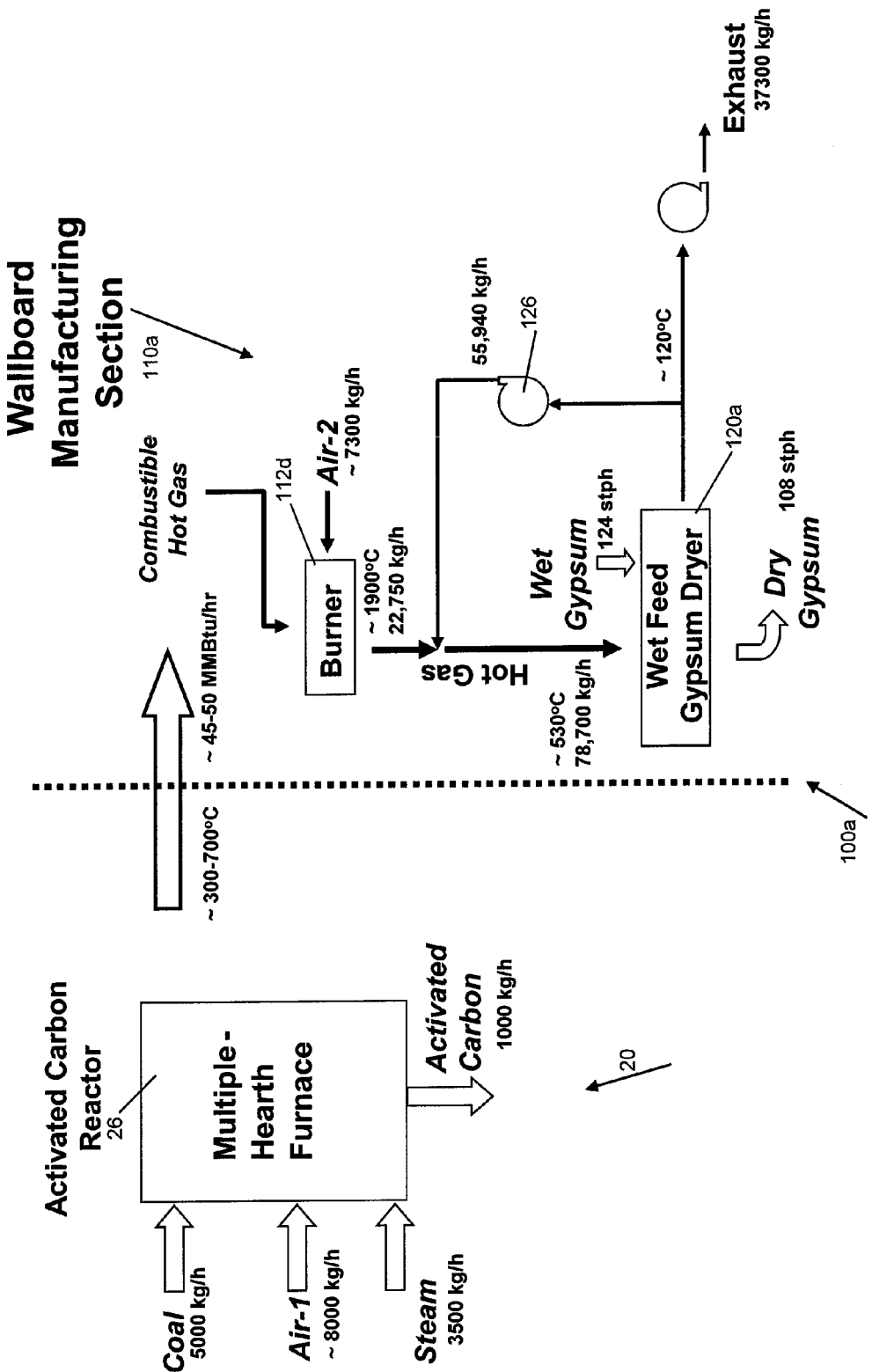
FIG. 5 is a schematic flow diagram of an integrated activated carbon and gypsum wallboard production plant that uses energy for gypsum drying according to the invention.
Figure 6:
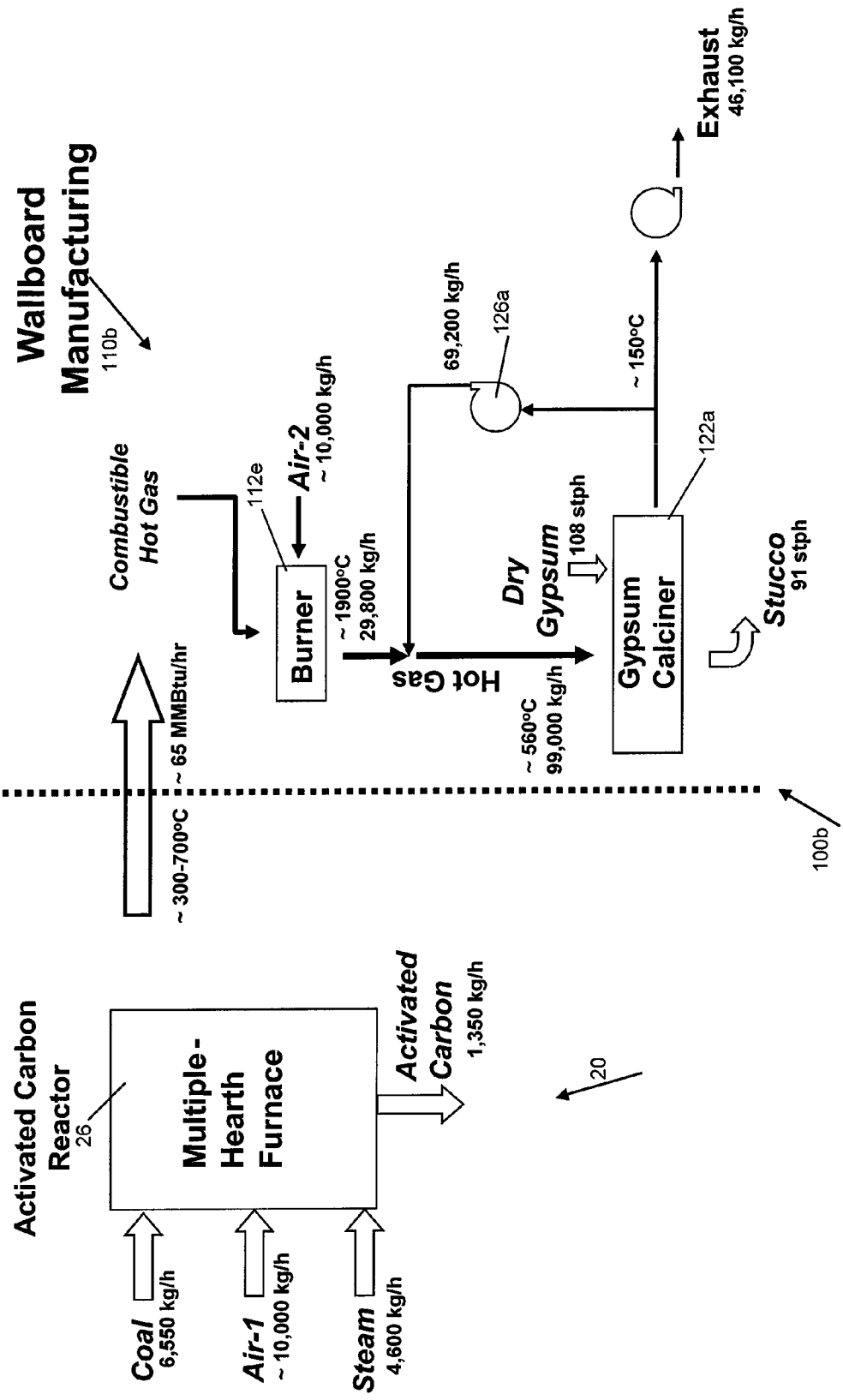
FIG. 6 is a schematic flow diagram of an integrated activated carbon and gypsum wallboard production plant that uses energy for gypsum calcination according to the invention.

FIG. 4 is one embodiment of the present disclosure of a system for an integrated activated carbon and wallboard production process plant. FIGS. 5 and 6 are detailed examples of this embodiment identifying the energy sharing between the activated carbon production reactor and the gypsum drying and gypsum calcination steps of wallboard production.

In the wallboard manufacturing process, raw gypsum (synthetic or mined) is first dried, for example in a cage mill, using hot process gas typically obtained from natural gas firing. The dried gypsum (land plaster) is then calcined to form Plaster of Paris ($CaSO_4.\frac{1}{2}H_2O$) or stucco. The temperature of calcination is around 300 to 350° F. Calcination is performed in an impact mill, where hot gases, typically produced from the combustion of natural gas, are contacted with the gypsum. Both size reduction and calcination are performed simultaneously to yield a fine calcined powder. Alternately, calcination can be performed in a kettle calciner, where the heat is transferred to the gypsum particles indirectly. To form the wallboard, the stucco is then mixed with water and other additives and discharged into a forming line. A portion of the water added to the slurry is consumed in formation and re-crystallization of gypsum in the wallboard. The "wet" board is then moved to dryer lines where the excess moisture is evaporated in a controlled manner.

As described above, wallboard production requires heat for various processing steps—up to 20% in the feed gypsum drying, another 25% in gypsum calcination, and about 55% in board drying. About 2 MMBtu/MSF (MSF=1000 $ft^2$) of wallboard is required for the overall production.

Production of Process Heat for Wallboard Manufacturing Plant Section (110) from the Combustion of Hot Combustible Product Gas from the Activated Carbon Production Plant In this combined activated carbon and wallboard co-production process (FIG. 4), at least a portion of the process heat required for the wallboard production is generated through the combustion of hydrogen-rich combustible product gas that is generated in the activated carbon production reactor.

In one embodiment, a portion of the hot combustible product gas from the activated carbon production reactor is directed to the burner (112) of the raw feed dryer. Combustion air is added to the burner to burn the fuel gases and generate a hot combusted product gas that can be contacted directly with the wet feed to evaporate the water and dry the gypsum material. The contacting of the hot gases and the wet gypsum can also be performed in a rotary kiln dryer (120) or any other type of drying equipment. To modulate the temperature of the hot gases contacting the wet gypsum, a recycle fan (126) may be used to re-circulate cold exhaust gases from the dryer (120a) exit to the front of the dryer or the burner (112d) as shown in FIG. 5.

In addition to the above, another portion of the hot combustible product gas from the activated carbon production reactor can be directed to the burner (112a) of the gypsum calciner (122) (FIG. 4). Combustion air is added to the burner to burn the fuel gases and generate a hot combusted product gas that can be contacted directly with the gypsum feed to calcine the gypsum and drive off the chemically bound water and form stucco. The contacting of the hot gases and the gypsum can be performed in an impact mill, where both calcination and grinding is performed. Alternately the hot gases can be used to transfer the heat to the gypsum in a kettle calciner where the heat is transferred to the gypsum in an indirect manner.

To modulate the temperature of the hot gases contacting the gypsum in the calciner, a recycle fan (126a) may be used to re-circulate cold exhaust gases from the calciner (122a) exit to the front of the calciner or the burner (112e) as shown in FIG. 6.

In addition to the above, another portion of the hot combustible product gas from the activated carbon production reactor can be directed to a boiler (112c) or hot oil heater (112b) and combusted to generate hot combusted gas (FIG. 4). In either of these devices, steam or "hot" oil is produced by transferring the heat from the combustion gases to process fluid. The "hot" steam and/or "hot" oil is directed to the board dryer (124), where the heat transferred to gases that are used to dry the wallboard. The steam and/or the "hot oil" act as a heat transfer fluid. In this manner, a clean gas stream can be used to dry the wallboard and contact with the "dirty" gases from the combustion of the hot combustible product gas from the activated carbon production reactor is prevented.

Process Control for Wallboard Manufacturing

In another embodiment, natural gas is used in combination with the combustible product gases from the activated carbon production reactor to enable control of the temperature of the hot gas mixture. The proportion of natural gas can be minimized and set at values just necessary for process control.

Co-firing of natural gas and activated combustible product gas from the activated carbon production reactor also enables "assured" process operation or back-up fuel in case the activated carbon production reactor (ACPR) has to be shut down.

Several exhaust gas streams in wallboard production are almost pure steam (moisture). For example, if an indirect kettle calciner is used for the production of stucco, the exhaust gases from the calciner is almost completely pure water vapor. This stream may be advantageously used as process gas for the activation step in the activated carbon production reactor.

Similar to the previous embodiment of the co-production of activated carbon and ethanol, the following advantageous aspects are included in the preferred embodiments of co-production of activated carbon and gypsum wallboard.

(i) Cooling of hot activated carbon product with moisture-rich gases from wallboard manufacturing (ii) Use of moisture-rich exhaust gases from the wallboard manufacturing as process feed gas for carbon activation in the activated carbon production reactor Removal of $SO_2$ Generated from the Combustion of Product Gas from the Activated Carbon Production Reactor In another embodiment of the invention, if the combined activated carbon and wallboard plant is located at a coal-fired power plant equipped with a wet flue gas desulfurization scrubber making gypsum for supply to the wallboard plant, the lime/limestone slurry from the coal-fired plant's scrubber system may be advantageously pumped via pipe-line to the wallboard production section of the co-production plant. A wet scrubber system may be employed to remove $SO_2$ from the process gases generated from the combustion of the hydrogen-rich product gas from the activated carbon production reactor using the lime/limestone slurry from the coal-fired power plant. The "used-up" slurry can be returned to the coal-fired plant wet scrubber system for additional processing (for example, oxidation to gypsum and separation). In this manner, capital equipment required for scrubbing $SO_2$ from the gases generated from the combustion of product gases can be minimized as the feed lime/limestone preparation and "used scrubber liquid" handling can be performed in an efficient manner with the coal-fired scrubber system.

EXAMPLES

Example 7

Integrated Wallboard and Activated Carbon Production Plant

An integrated wallboard and activated carbon production plant with the identified improvements (FIGS. 4, 5 and 6) and advantages relative to stand-alone plants is described below.

Coal (lignite) of the composition identified in previous examples is used as feed stock. The production of process heat for drying the raw "wet" gypsum feed section of the process is performed in the following manner (FIG. 5). About 5000 kg/hour of coal is introduced into a multiple hearth furnace. About 8000 kg/hour air and 3500 kg/hour steam is introduced in the various hearths of the MHF to generate the heat required and provide the optimum gaseous environment for the production of activated carbon. About 1000 kg/hour of activated carbon is produced from this reactor set-up. The hot combustible product gases leaving the multiple hearth furnace (activated carbon production reactor) at the top is sent to the gypsum dryer burner in the wallboard plant. Additional air is added to the burner (Air-2-7300 kg/hour) to completely combust the hydrocarbons to yield an approximately 1900° C. hot gas. This is mixed with the cold exhaust to generate process hot gas of at about 78,700 kg/hour at 530° C. The amount of heat supplied by this hot gas is sufficient to dry 124 short tons per hour of approximately 10% moisture raw gypsum feed.

The production of process heat for the gypsum calcining section is performed in the following manner (FIG. 6). An additional of about 6550 kg/hour of coal is introduced into the multiple hearth furnace along with about 10000 kg/hour air and 4600 kg/hour steam to produce an additional 1350 kg/hour of activated carbon from this reactor set-up. The hot combustible product gases leaving the multiple hearth furnace at the top is sent to the gypsum calciner burner in the wallboard production section of the co-production plant. Additional air is added to the burner (Air-2-10000 kg/hour) to completely combust the hydrocarbons to yield an approximately 1900° C. hot gas. This is mixed with the cold exhaust to generate process hot gas of at about 99,000 kg/hour at 560° C. The amount of heat supplied by this hot gas is sufficient to calcine 108 short tons per hour of dry gypsum feed to yield 91 short tons of stucco.

The activated carbon production reactor can be sized to provide enough combustible process gas for feed drying, calcination and board drying steps of wallboard production—and splitting the product gas to direct to each end application.

IV. Co-Production of Activated Carbon and Cement:

Cement manufacturing generates about 2 tons of $CO_2$ for every ton of cement clinker of produced. Half of the $CO_2$ produced is from the combustion of the fuel required for the clinkering and calcination process. There is a need to reduce $CO_2$ emissions from cement clinker manufacturing.

Figure 7:
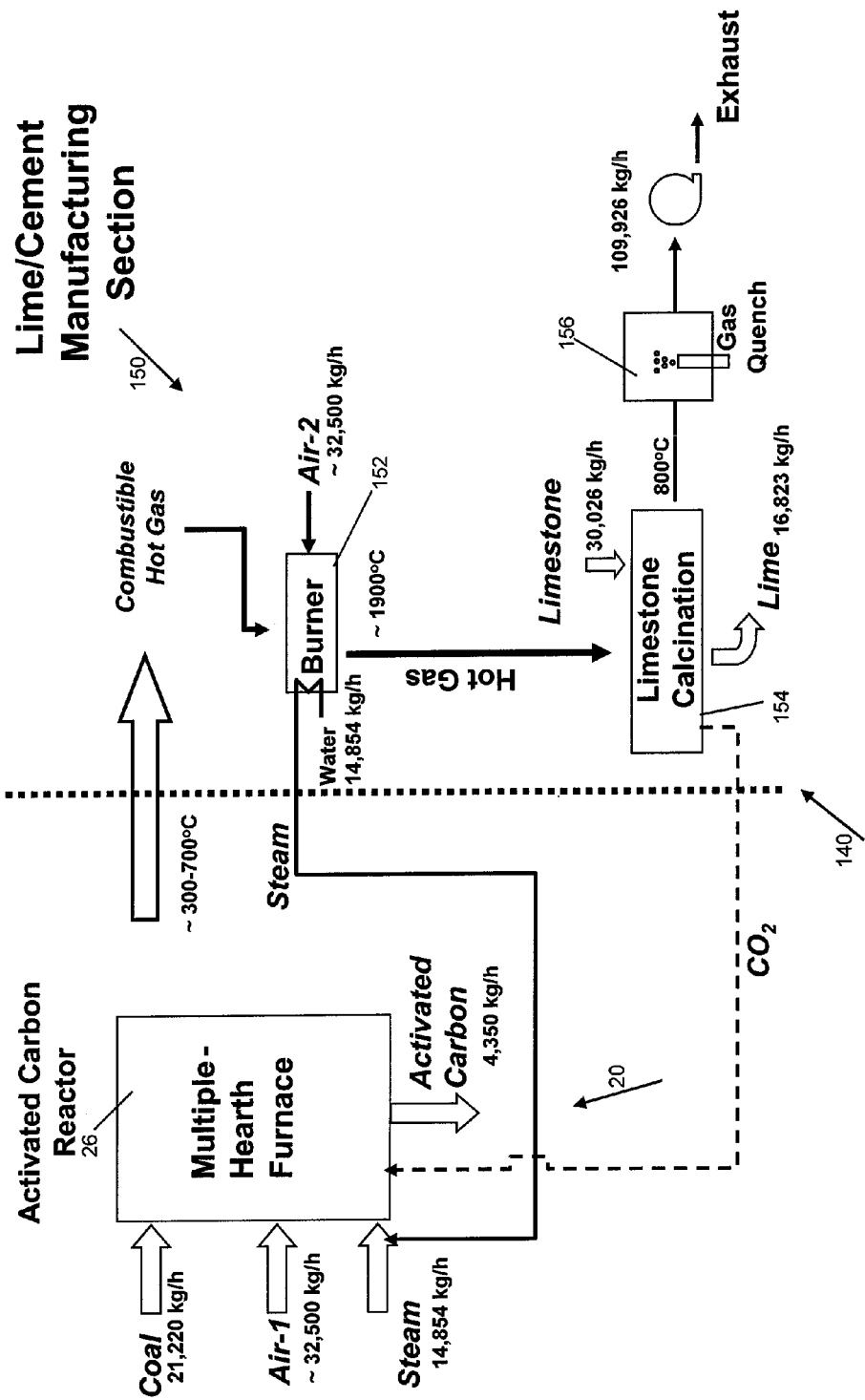
FIG. 7 is a schematic flow diagram of an integrated activated carbon and cement production plant according to the invention.

In this embodiment (FIG. 7), activated carbon and cement/lime is co-produced in the co-production plant (140). The combustible product gases from the activated carbon production reactor (26) from the activated carbon manufacturing section of the plant (20) are directed to the cement manufacturing section of the plant (150). There, the combustible gases are advantageously combusted in either the cement clinkering kiln or in the pre-calciner section (154) (FIG. 7), with the energy used to calcine limestone ($CaCO_3$) to lime (CaO). The combustible gases are advantageously combusted in a burner (152) prior to or while contacting the limestone. In this manner, a lower carbon/hydrogen ratio fuel is used for process heat compared to the entire coal thus reducing the overall $CO_2$ emissions from cement/lime manufacturing section (150). Again, as described in previous embodiments, the carbon-dioxide rich flue gases from cement manufacturing may be used as reaction process gas in the activation section of the activated carbon production reactor. If steam is required for activation instead of carbon dioxide, then a portion of the energy in the hydrogen-rich combustible gases may be advantageously used for steam generation in a boiler (152), which may be combined with the hydrogen-rich combustible gas burner. The exhaust from the calciner is typically at high temperatures and is typically cooled (for example, by water quench) in the gas cooler (156) before it is cleaned and exhausted.

Example 8

Integrated Cement and Activated Carbon Plant

The energy content in the coal used is about 6400 Btu/lb and the total energy content coming into the process with the coal is 300 MMBtu/hr (21,220 kg/h or 46,680 lb/h coal). The energy content leaving the process with the activated carbon is about 99 MMBtu/hr. The remainder is about 200 MMBtu/hr and is the energy content of the hydrogen-rich combustible gases. The amount of limestone calcined is 30,026 kg/h. The amount of energy required for limestone calcination (heating to 800° C. and heat of calcination) is 75 MMBtu/hr which is about 38 percent of the energy content of the hydrogen-rich (carbon-deficient) combustible gases. The energy required for water evaporation for the process (activation) corresponds to about 14,854 kg/h (32,700 lb/h) or about 33 MMBtu/hr. This corresponds to another 16 percent of energy utilization or a total of about 50 percent utilization of the energy in the hydrogen-rich combustible gases. This process example has a lower utilization efficiency compared to previous examples because the heat delivery has to occur at a high process temperature (800° C. for calcination).

Other embodiments of this invention may be accomplished in a method and system for co-producing a product (such as upgraded coal or biomass) in an energy consuming process and a carbon-rich product (such as activated carbon) from a hydrocarbon material such as coal or biomass. This is performed by directing the hydrogen-rich (carbon-deficient) combustible gases from the activated carbon production reactor and using its energy content by combusting it and using the released energy to a high efficiency in the energy consuming steps of manufacturing of the co-product.

Figure 8:
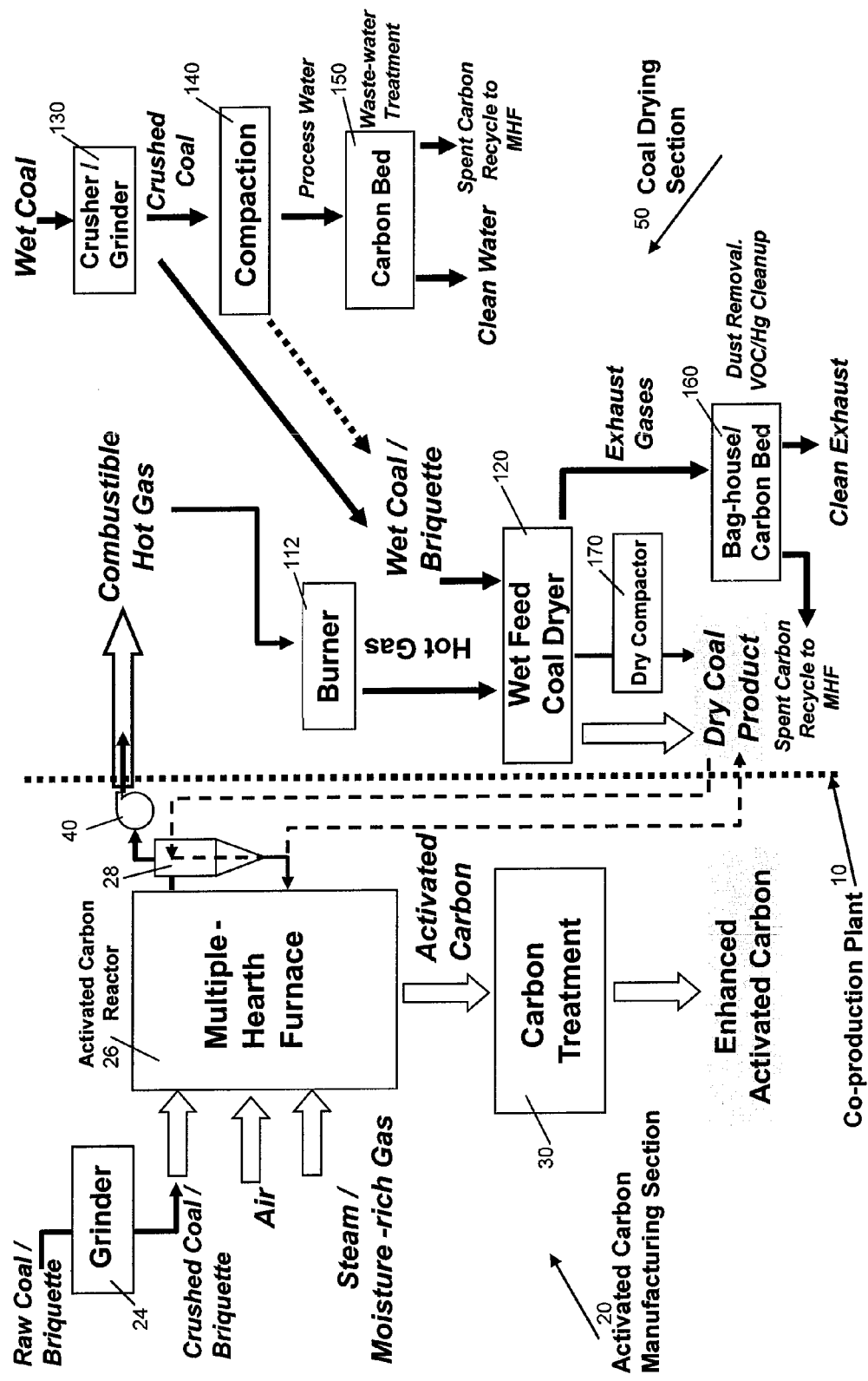
FIG. 8 is a schematic flow diagram of an integrated activated carbon and dried upgraded coal production plant according to the invention.

These preferred embodiments are described below.
V. Activated Carbon and Upgraded/Dried Coal Co-Production (Single stage Drying)
Activated Carbon Production from Hydrocarbon Feedstock and Production of Lower C/H Ratio Hot Combustible Product Gas than Parent Feedstock In this method (FIG. 8) activated carbon and an upgraded/dried coal product are produced in co-production plant (10).

Activated carbon is produced in the activated carbon manufacturing plant section (20) by carbonizing a solid or partially solid (e.g. wet) carbonaceous material to yield a carbonized product and carbonization product gases; activating the carbonized product with steam or carbon dioxide to yield activated carbon and activation product gases; such that the combination of the carbonization product gases and the activation product gases (hydrogen-rich hot combustible product gases from the activated carbon reactor) have a lower carbon-to-hydrogen (C/H) ratio compared to the parent carbonaceous material. In the above method carbonizing or pyrolysis is typically performed at 400 to 600° C. and activation with steam is performed at 700 to 1000° C.

Activated carbon produced by the above method has a surface area of at least 200 $m^2$/gm, preferably at least, 300 $m^2$/gm, and more preferably at least 400 $m^2$/gm. Surface areas are determined by the Brunauer-Emmett-Teller $N_2$ adsorption method.

A multiple hearth furnace (MHF) may be used as the activated carbon production reactor (26). Coal or other carbonaceous feedstock is prepared via hammer mills (24) to about ⅛" to ½" in size and introduced to the top of the activated carbon production reactor. The carbonaceous material goes through a series of steps including drying, devolatilization and activation in the MHF to product activated carbon. The hot gases leaving the activated carbon production reactor contain fine particulate. The fine particulate, which is partially processed material, is collected in a cyclone (28) and advantageously returned to the reactor for further processing.

The hot gases leaving the activated carbon production reactor also contain condensable tar. In one embodiment of the process, the hot gases are contacted with "dry" coal product (from the coal dryer section) in cyclone (28) to lower the temperature of the gases and condense the tar onto the coal particles. In another embodiment of the process, a second cyclone or a contacting device may be disposed after cyclone (28) to perform the contacting. The proportion of "dry" coal (from the coal drying section) used is expected to be a function of the amount of tar present in the fuel gas and it is preferred that the tar/"dry" coal ratio is maintained less than about 5 percent to ensure a flowable product. For a 5000 kg/hr coal feed to the activated carbon reactor, and assuming a 5 percent conversion of coal to condensable tars (250 kg/h), one would need to contact the hot gases leaving the activated carbon production reactor with more than about 5000 kg/hr of "dry" coal from the coal drying section to result in a non-sticky flowable product. In another preferred embodiment, the hot gases leaving the activated carbon production reactor and containing tar are contacted with "wet" coal. The sensible heat in the reactor exit gases can be beneficially used to evaporate the moisture in the coal, while simultaneously lowering the temperature of the combustible gases and depositing and solidifying the tar on the coal. It is advantageous to cool the combustible gases to a temperature in the neighborhood of 300° F., to facilitate low power requirements for pumping and ease of handling. The "dried" coal generated in the above manner is then separated from the combustible gases either in a cyclone or another particulate separation device. The resulting combustible gases are cooled relative to their exit from the activated carbon production reactor and are also stripped of their tar content. This facilitates and enables the transport of the combustible gases over long ducts to other portions of the combined plant without the risk of fouling of those ducts and tar buildup. This also provides greater flexibility on the location where the combustible gases can be combusted for heat supply to the companion process. In other preferred embodiments, contacting with a combination of "dry" and wet coal/ biomass can also be used to lower the temperatures of the combustible gases from the activated carbon production reactor and to capture and solidify the tar.

Chemical activation of the carbonaceous feedstock instead of physical activation may also be used. In chemical activation, the carbonaceous material is mixed with a dehydrating agent such as zinc chloride, phosphoric acid or alkali hydroxide such as potassium hydroxide. This is followed by heat treatment to temperatures between 450 and 900° C. to carbonize the material and release hot combustible product gases.

Activated carbon made by the above method can be further processed in the carbon treatment unit (30) by grinding to a fine powder to less than 30 microns in mean particle size and preferably to less than 10 microns in mean particle size. The activated carbon made by the above method may also, in addition, be impregnated with halogens such as bromine or bromine compounds, such as ammonium bromide, to form enhanced activated carbon. Such enhanced activated carbon is advantageously used as sorbents for mercury removal from coal-fired power plant flue gases as is well known in the art.

In this first embodiment, the co-product manufactured through one or more energy consuming steps is an upgraded/dried coal. In the coal drying section (50) of the process (FIG. 8), raw wet coal is first crushed to an appropriate size (typically less than 1 inch) in crusher (130) and fed to a coal drying reactor or chamber (120). The dried coal product from the coal dryer may be further compacted in a dry material compaction device (170) for purposes of improving the transporting and handling characteristics of the dry coal product. The compaction device is one known in the art, where high pressures are used to collapse the pores within the coal matrix, thus preventing infiltration of air and oxidation during storage and handling.

Alternately, the raw wet coal is first crushed to an appropriate size (typically less than 1 inch) in crusher (130) and fed to a compaction device (140) and the wet briquette fed to the coal dryer (120). The compaction device can be a roll press, where the material passes between two rollers spaced only a short distance apart relative to the input coal size. Compaction pressures of at least 5000 psi and up to 100,000 psi may be used to compress the wet coal, collapse the pores within the coal matrix and "squeeze" out the water trapped within the pores. The compaction step may be repeated several times to remove additional moisture within the coal matrix. The resulting products are a "drier" coal and squeezed out water. The compacted and dried coal may be used as a "dry" product (not shown) as is or further dried to remove the surface moisture in a coal dryer (120). The water stream from the compaction device (140) may contain some organics from the coal as well as some inorganic impurities. The water stream can be cleaned with methods known in the art of wastewater treatment. In one embodiment, the water treatment step includes mixing it with activated carbon and separating the activated carbon or passing it through an activated carbon bed (150) to remove organic and other impurities. The spent activated carbon can be advantageously recycled to the activated carbon reactor (26).

Production of Hot Combusted Gas for Wet Coal Drying from the Combustion of Combustible Product Gas from the Activated Carbon Production Plant In this embodiment of the inventive process, activated carbon and dry coal product are co-produced in a plant (FIG. 8), and at least a portion of the process heat required for the coal drying section of the plant is produced through the combustion of hydrogen-rich combustible gas generated in the activated carbon production reactor. The burner/combustor (112) is one known in the art and typically comprises a burner and combustion chamber. The hot combusted gases may be attemperated by mixing with cold air or with recycled cold exhaust gas from the drying plant section before being used in the coal dryer.

The coal dryer (120) can one of many types that are known in the art. The coal dryer can be a direct contact dryer, where the wet crushed coal or wet briquettes are contacted directly with the hot combusted or attemperated gases from the burner/combustor (112)—see FIG. 8. The direct contact dryer could be a flash drier, where the "wet" coal particles or crushed briquettes are entrained with the hot gases, evaporating the water/moisture associated with the coal and transferring it to the gaseous phase. The dried coal is then separated in a first particulate separation device consisting of a cyclone or multiple cyclones and the exhaust gases from the first particulate separation device cleaned further in a second particulate removal device such as bag-house or electrostatic precipitator. The second particulate removal device may be combined with a dry scrubber with lime injection for $SO_2$ control and/or activated carbon injection for mercury removal from the exhaust gases as is known in the art. Alternately, the direct contact coal dryer could be rotary kiln where the wet coal/briquette size is relatively large and the velocities in the kiln are relatively low such that the dried coal is not entrained and is removed via gravity at the kiln exit. The exhaust gases, along with the evaporated moisture, are cleaned as described in the aforementioned fashion, for example with a bag-house.

Alternatively, the coal dryer can be indirect contact dryer. In this case, the hydrogen-rich combustible gases from the activated carbon reactor can be directed to a burner-combustor-boiler (steam generating unit), where the sensible and chemical energy in the combustible product gases from the activated carbon production is converted by reacting with air (combustion), and the hot gases generated from combustion used to make steam at a temperature and pressure that would be adequate for utilization in the energy consuming steps of coal drying. Alternatively, or in addition, combustible gases can be directed to a furnace [e.g., heat transfer fluid (oil) heating unit)] where the sensible and chemical energy in the product gases from the activated carbon production is converted to heating a "non-contact heat transfer fluid" that would be adequate for utilization in the energy consuming steps of coal drying. In both of the above cases, the steam/"hot" oil is used to transfer its energy to the wet parent hydrocarbon feed indirectly to evaporate the moisture in the parent hydrocarbon and generate a "dried" hydrocarbon material that has a higher energy content per unit mass. The indirect coal dryer can be a rotary kiln with a shell that is heated with the steam or the "hot" oil. Alternately, the indirect coal dryer could be a fluidized bed embedded with steam coal or "hot" oil coils. Wet coal would be fed to the fluidized bed and the heat in the steam/"hot" oil transferred through the tube walls to the coal to drive off the moisture. Methods well understood in the art can be used to separate the evaporated moisture from the dried coal.

In all of the above cases, the flue gas generated from the combustion of activated carbon reactor product gases has a lower $CO_2$ content per unit of heat generated than direct combustion of the feed coal or biomass.

Cooling of Hot Activated Carbon Product with Moisture-Rich Gases from Coal Dryer Section Activated carbon leaving the bottom of the activated carbon production reactor, such as a MHF is at a high temperature, typically around 1500 to 1700° F. This hot material is typically cooled with an indirect heat exchanger before being discharged. In an embodiment of the invention, the hot activated carbon product is advantageously cooled with moisture-rich gas stream from the coal dryer section of the plant, in particular the clean exhaust leaving the bag-house/carbon (160) bed of the coal dryer section, in a heat exchanger (not shown). The heat exchanger can be of an indirect contact type, or a direct contact heat exchanger. If direct contact heat exchange is used, the gas streams should have a maximum of about 1 percent $O_2$, preferably less than 0.5% $O_2$ to prevent oxidation and degradation of the activated carbon product. The heat exchanger is preferably operated in a predominantly counter-current mode, with the hot activated carbon product and the "cooling" gas streams flowing in a counter-current fashion. The heated (moisture-rich) gas stream can then be advantageously used subsequently as process gas in the activation step of the activated carbon plant.

Use of Moisture-Rich Exhaust Gases from the Coal Dryer Section of the as Process Feed Gas for Activation in the Activated Carbon Production Reactor In another embodiment of the combined activated carbon and coal drying plant, at least a portion of the exhaust gas streams in the coal drying section of the plant that has very high moisture content is used as activation process gas. For example, if an indirect steam-driven dryer is used for the drying process, the exhaust gases from the dryer (from the drying process) are almost completely pure water vapor. This stream may be advantageously used as process gas for the activation step in the activated carbon plant. This gas stream may be advantageously preheated as described in the preceding paragraphs before introduction into the activation section of the activated carbon plant. By using the moisture-rich stream from the coal drying section in the activated carbon plant, water and energy consumption for the combined plant is reduced, since steam required for the activation step in the activated carbon plant does not have be raised separately.

The flue gas from the combustion of the hydrogen-rich (carbon-deficient) combustible gas produced by the activated carbon reactor is treated to reduce the concentration of various pollutants in a manner that is known in the art. For example, ammonia can be injected in the flue gases at a temperature of about 1500-1800° F. to reduce the nitrogen oxides to molecular nitrogen. Alkaline material, such as lime slurry can be injected into the flue gas after it has been used for drying and its temperature lowered to capture sulfur oxides, and the coal ash and scrubber particulate can be removed using a dust collector such as a fabric filter (160).

Use of "Dry" Coal Product as Feed for the Activated Carbon Production Reactor

In an alternate embodiment, instead of wet coal as feed to the activated carbon manufacturing section (20), a drier coal is used as feed. In one embodiment, a portion of the dry coal product from the wet feed coal dryer (120) in the coal drying section (50) is routed to the grinder (24) in the activated carbon manufacturing section. In another embodiment, a portion of the dry compacted coal product from the dry compactor (170) is routed to the grinder (24). In yet another embodiment, a portion of the partially dewatered briquette from the compaction device (140) is routed to the grinder (24) and as feed to the activated carbon reactor (26). In all of the above cases, the use of a dry feed to the activated carbon production section results in less heat duty requirements in that section and a higher production throughput of activated carbon product for a given size reactor (26).

Co-Firing of Coal and Hot Combustible Product Gas from the Activated Carbon Production Plant for Coal Drying In an alternate embodiment, if the coal drying section of the plant requires more energy than what is provided by the combustion of the hydrogen-rich combustible gas from the activated carbon reactor, supplemental firing of additional fuel may be used. This additional fuel can be coal, preferably, or an alternate fuel, such as natural gas.

The hydrogen-rich combustible gas from the activated carbon production reactor may be fired simultaneously with the supplemental fuel in an advantageous manner to reduce pollutant emissions such nitrogen oxides. For example, the hydrogen-rich combustible gas may be preferentially introduced in a reducing zone of the combustor, followed by staged addition of combustion air into the combustor to minimize nitrogen oxide formation and complete combustion. Alternately, the combustible product gas can be introduced into the combustor as a "re-burn" fuel at a downstream location of the combustor to reduce nitrogen oxides formed upstream in the combustor.

Boosting Pressure of the Hot Combustible Product Gas from the Activated Carbon Plant Depending on the operation of the activated carbon reactor, the hydrogen-rich combustible gas from the reactor may need to be delivered at a higher pressure to downstream components/devices than made available at the exit of the reactor. A higher pressure may be required, for example, to obtain better distribution of the combustible gas within a downstream device. In such cases, a fan (40) that can handle hot and particulate-laden gas streams may be used. If the combustible gas from the activated carbon plant has too high a temperature for it to be effectively handled by a fan, then it may be cooled down to the necessary temperature before its introduction into the fan. Cooling may be achieved with a heat exchanger or by mixing in a cold gas stream.

Destruction of Volatile Organic Compounds in Exhaust Streams from Coal Drying Section in the Activated Carbon Production Plant or the Burner/Combustor The coal dryer section may emit volatile organic compounds (VOC). To prevent emission of VOC into the environment, these streams may be advantageously routed to the bag-house/carbon bed (160), where the organic compounds may be captured by the carbon. The spent carbon may be recycled to the activated carbon reactor (26) or the burner/combustor (112) for VOC destruction.

Removal of Condensable Tars from the Activated Carbon Reactor Product Gases

The devolatilization of coal releases tars that are carried out of the activated carbon production reactor with the combustible gases. Theses gases have to be maintained at a relatively high temperature to prevent condensation of the tars and equipment fouling. It also requires that the burner/combustor for oxidizing the combustible gases be physically closely coupled to the activated carbon production reactor. In a preferred embodiment, the dry coal product from coal dryer (120) (see FIG. 8) is mixed with the combustible gases in a mixing and separation device such as cyclone (28) or in a cyclone or other mixing device downstream of the cyclone (28). The combustible gases are advantageously cleaned of their tar content, allowing for their transport and handling without the risk of downstream equipment fouling. The dry coal product is also enhanced as it covered with hydrophobic tar material making it less susceptible to oxidation and wetting.

In another preferred embodiment, the hot gases leaving the activated carbon production reactor and containing tar are contacted with "wet" coal. The sensible heat in the reactor exit gases can be beneficially used to evaporate the moisture in the coal, while simultaneously lowering the temperature of the combustible gases and depositing and solidifying the tar on the coal. The "dried" coal generated in the above manner is then separated from the combustible gases either in a cyclone or another particulate separation device. The resulting combustible gases are cooled relative to their exit from the activated carbon production reactor and are also stripped of their tar content. This facilitates and enables the transport of the combustible gases over long ducts to other portions of the combined plant without the risk of fouling of those ducts.

EXAMPLES

Example 9

Figure 9:
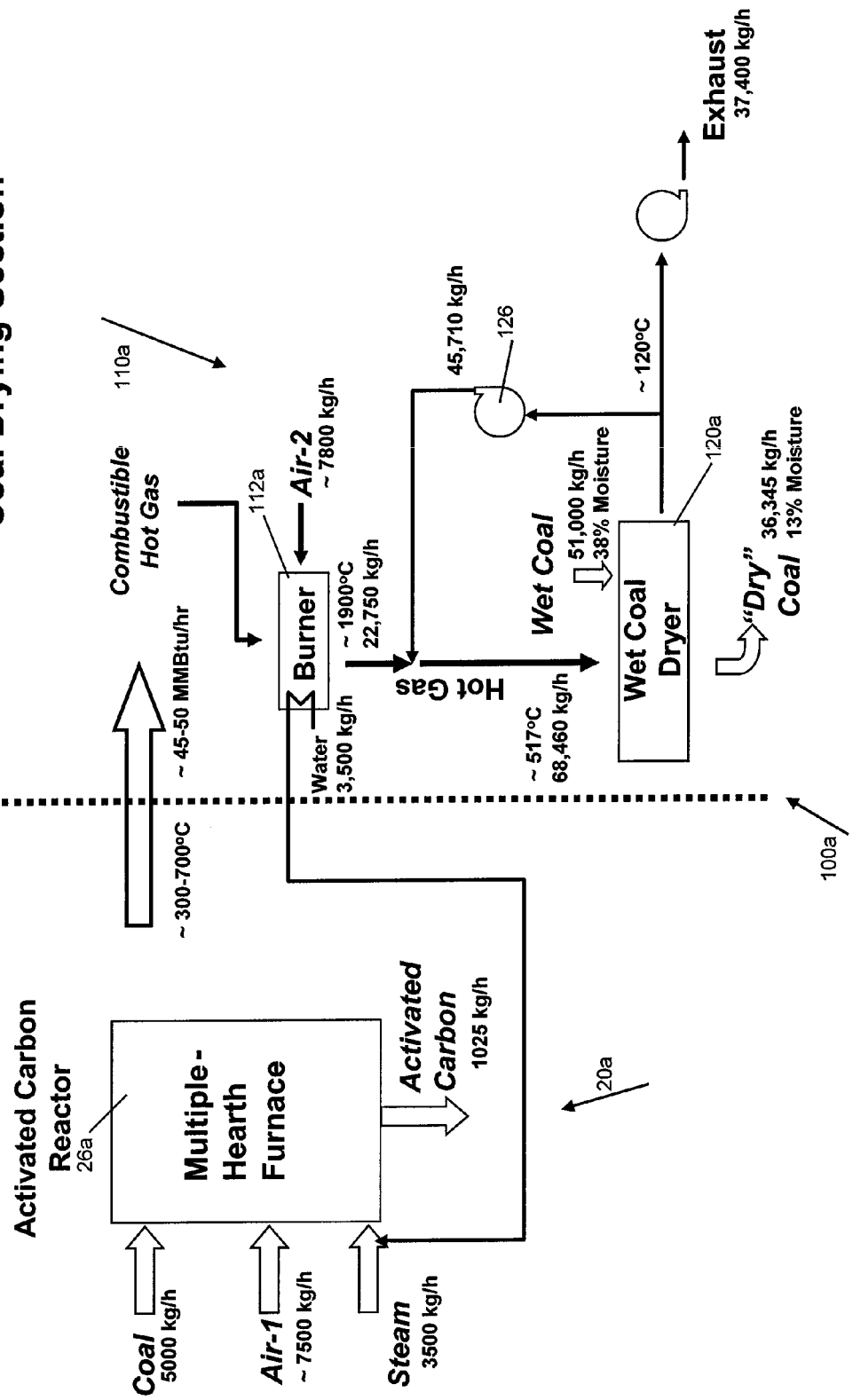
FIG. 9 is a schematic flow diagram of a process for the co-production of activated carbon and upgraded "dried" coal using thermal drying of the raw coal according to the invention.

Thermal/Flash Drying of Wet Coal to Produce "Dry" Coal and Activated Carbon Production An activated carbon production and "dry" coal production (using a thermal/flash drier) plant with the identified improvements (FIG. 9) and advantages relative to stand-alone plants are described below.

Coal (lignite) of the composition provided below is used as feed stock for activated carbon.

| | Composition | wt-% |
|---|---|---|
| C | Carbon | 34.6 |
| H | Hydrogen | 3.5 |
| S | Sulfur | 0.61 |
| O | Oxygen | 21.6 |
| N | Nitrogen | 0.66 |
| | Ash | 7.0 |
| $H_2O$ | Moisture | 32.0 |

Activated carbon is produced in the activated carbon manufacturing section (20a). Yield from the activated carbon production reactor (26a) is about 20-30 percent based on wet feed input. For a 5,000 kg/hour wet lignite input, this plant yields about 1,025 kg//hour (20 percent yield) of activated carbon product.

A typical activated carbon composition is shown below obtained from processing the above-described feed stock in the proposed inventive method.

| | Composition | wt-% |
|---|---|---|
| C | Carbon | 68 |
| H | Hydrogen | 0.5 |
| S | Sulfur | 1.5 |
| O | Oxygen | 0.5 |
| N | Nitrogen | 0.7 |
| | Ash | 28.0 |
| $H_2O$ | Moisture | 1.0 |

The elemental composition of the combustible gases prior to any partial oxidation or steam reforming is given below:

| | Composition | wt-% |
|---|---|---|
| C | Carbon | 26.3 |
| H | Hydrogen | 4.3 |
| S | Sulfur | 0.4 |
| O | Oxygen | 26.9 |
| N | Nitrogen | 0.7 |
| | Ash | 1.8 |
| $H_2O$ | Moisture | 40.0 |

The heating value of the wet coal (lignite) with the composition provided above is about 14.8 MJ/kg on a lower heating value basis. The $CO_2$ emissions from the combustion of 1 kg of coal is calculated to be 1.27 kg, thus resulting in 11.7 MJ of heat released per kg of $CO_2$ emitted. In contrast, the heating value of the combustible gases (prior to composition and energy changes from partial oxidation or steam reforming in the activated carbon production reactor) is estimated to be 12.8 MJ/kg on a lower heating value basis. The $CO_2$ emission from the combustion of these gases is calculated to be 0.96 kg, resulting in 13.3 MJ of heat released per kg of $CO_2$ emitted. The combustible gases represent a less $CO_2$-polluting fuel stream compared to the parent coal.

In addition to activated carbon, the activated carbon reactor produces hydrogen-rich combustible product gas which is sent to the coal drying section (110a) of the co-production plant (100a). A higher moisture (38 weight % $H_2O$) coal is used as feed stock for the coal drying section (110a) in the proposed inventive method. Wet coal is fed to the coal dryer (120a). The "dry" coal product from the dryer has a lower moisture content compared to the wet coal feed. 51,000 kg/hour of wet coal having a moisture content of 38 weight percent is dried using the heat from combusting the hydrogen-rich syngas from the activated carbon reactor to generate a 36,345 kg/hour of "dry" coal product having a moisture content of 13 weight percent. Based on the moisture content of the raw coal and "dry" product, about 1.4 kg of raw wet coal is required to produce 1.0 kg of "dry" coal product in this example.

Steam requirement for activation for the activated carbon production plant is about 0.7 kg of steam per kilogram of wet feed. For a 5,000 kg/hour wet lignite input, this translates to about 3,500 kg/hour of steam. In addition to predominantly providing the heat for coal drying, in this example, a small portion of the energy from the combustion of the hydrogen-rich combustible product gas from the activated carbon reactor is also used to generate steam for the activation process. The steam generating unit, i.e. boiler (not shown) is attached to the burner/combustor unit 112a and generates steam for the activated carbon reactor (26a).

The hot combusted gas from the burner/combustor/boiler (112a) has a very high temperature. It is attemperated advantageously with recycled exhaust from the wet coal dryer/baghouse (120a). Recycle fan (126) is used to transport the cool exhaust gas to mix with the hot combusted gas from the burner/combustor (112a). In this example, about 45,710 kg/hour of 120° C. exhaust gas is re-circulated to mix with hot combusted gas to generate 68,470 kg/hour of attemperated hot gas as feed to the coal drying unit (120a).

The flue gas generated from the combustion of activated carbon reactor product gases has a lower $CO_2$ content per unit of heat generated than direct combustion of the feed coal or biomass. For example, in the above example 3,803 kg/hour of $CO_2$ with a $CO_2$ content of 5.13 volume percent in the exhaust gas is generated for the required amount of steam for the activated carbon production and hot gases for coal drying. This compares to 3,867 kg/hour of $CO_2$ (6.21 volume percent in exhaust gases) with direct coal combustion is used for coal drying (see comparative Example 12 below).

The energy content in the coal used is about 6400 Btu/lb and the total energy content coming into the process with the coal is (5000 kg/hr or 11,000 lb/hour-70.4 MMBtu/hr. The energy content leaving the process with the activated carbon is about 22 MMBtu/hr. The remainder, excluding heat loss to the environment, is about 48 MMBtu/hr and is the energy content of the hydrogen-rich combustible gases. The energy used to dry the coal and evaporate the steam for the activated carbon reactor (3,500 kg/hour) is about 40 MMBtu/hr. The efficiency of energy utilization is about 83 percent.

The total amount of coal used for an integrated coal drying and activated carbon plant is 5,000 kg/hour to the carbon production reactor and 51,000 kg/hour to the coal dryer. This produces 36,345 kg/hour of "dry" coal product and 1025 kg/hour of activated carbon product. In comparison, a separately located coal-fired coal dryer and a coal-fed activated carbon plant with flue gas quench would require a total of 5000 kg/hour for carbon production and 3,050 kg/hour of coal to be burnt for drying the coal. The total $CO_2$ emissions from separately located plants would be 7,670 kg of $CO_2$/hour compared to 3,803 kg of $CO_2$/hour for an integrated plant. Even if the separate activated carbon production plant is equipped with recovering the excess heat and converting it to electricity, the efficiency of conversion is only about 20 to 25 percent (Example 13) compared to about 83 percent for the integrated coal drying-activated carbon plant.

Example 10

Co-Production of Activated Carbon and "Dry" Coal Using Wet Coal Compaction Followed by Briquette Drying An activated carbon production and "dry" coal production (using compaction followed briquette drying) plant with the identified improvements (FIG. 10) and advantages relative to stand-alone plants are described below.

Figure 10:
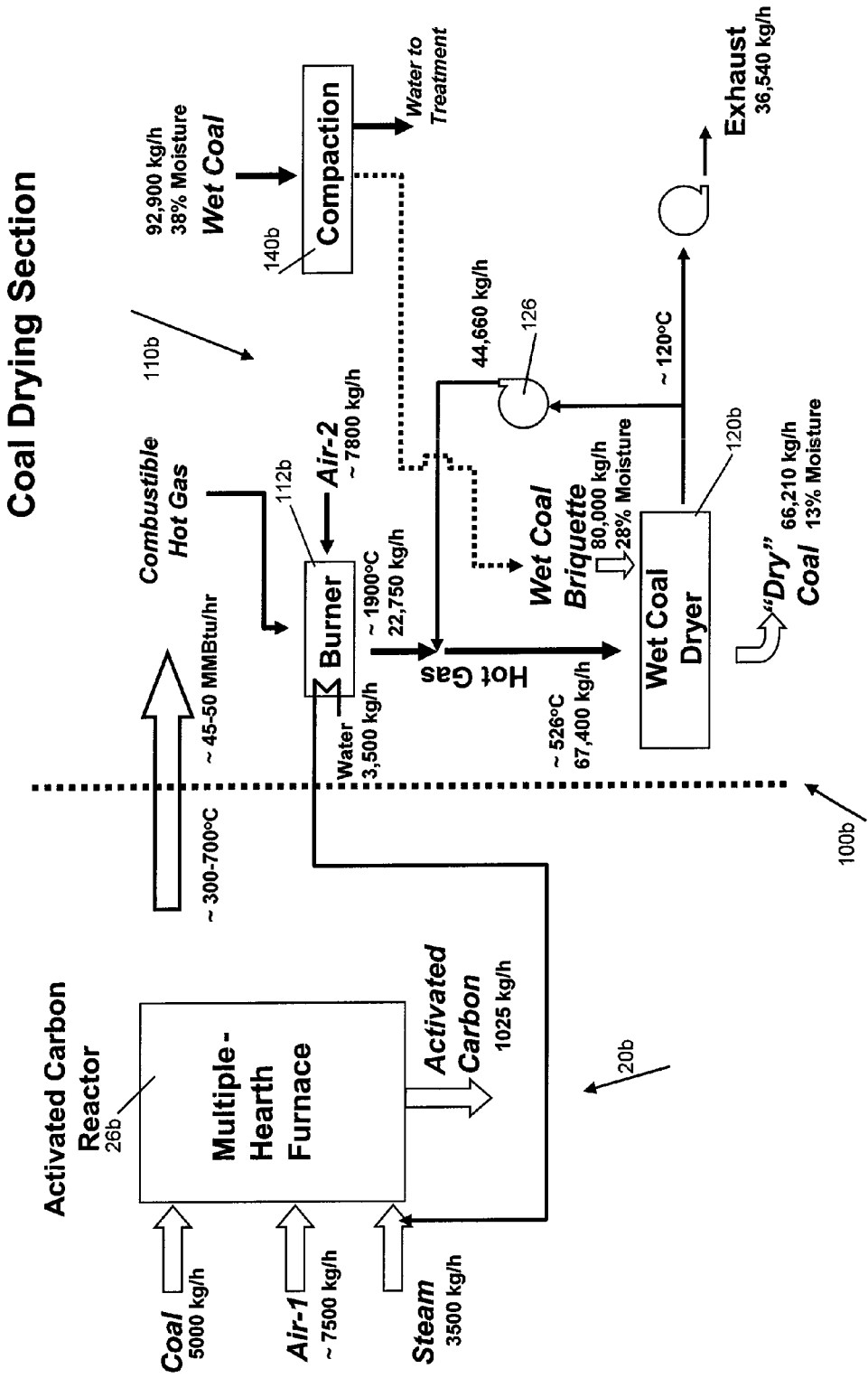
FIG. 10 is a schematic flow diagram of a process for the co-production of activated carbon and upgraded "dried" coal using compaction followed by drying of the raw coal according to the invention.

Coal (lignite) of the composition provided in Example 9 is used as feed stock for activated carbon. A higher moisture (38 weight % $H_2O$) coal, similar to Example 9, is used as feed stock for the coal drying section (110b) in the proposed inventive method (FIG. 10). In this method, the compaction step reduces the moisture content of the coal from 38 percent to 28 percent in the compaction device. Consequently, a lower initial moisture content coal briquette is fed to the coal dryer (120b) from the compaction device (140b). If the amount of energy transferred in the hydrogen-rich combustible syngas from the activated carbon manufacturing section (20b) is the same as in Example 9, a larger quantity of partially dewatered coal briquettes can be dried to the final moisture content of the dry coal product as in Example 9.

In this case, the corresponding flows that satisfy the overall energy balance are 92,900 kg/hour of wet coal feed to the compaction device (140b) resulting in 80,000 kg/hour of material with a moisture content of 28 weight percent, which when fed to the coal dryer (120b) produces 66,210 kg/hour of dry coal product with a moisture content of 13 weight percent. A higher throughput of dry coal product is achieved with the same energy supply from the activated carbon production reactor compared to Example 9 because only a portion of the moisture in the wet coal has to be evaporated; the rest is removed as liquid water in the compaction device. The corresponding $CO_2$ emissions and energy efficiency are identical to Example 9 and are dramatically improved in relation to comparative examples (12, 13 and 14) described below.

Example 11

Co-Production of Activated Carbon and "Dry" Coal with Thermal/Flash Drying and High-Moisture Gas Recycle to Activated Carbon Furnace An activated carbon production and "dry" coal production (using thermal drying only) plant (100c) with recycle of high-moisture content gas from the exhaust of the dryer (120c) to the activated carbon reactor (26c) and other identified improvements (FIG. 11) and advantages relative to stand-alone plants are described below.

Figure 11:
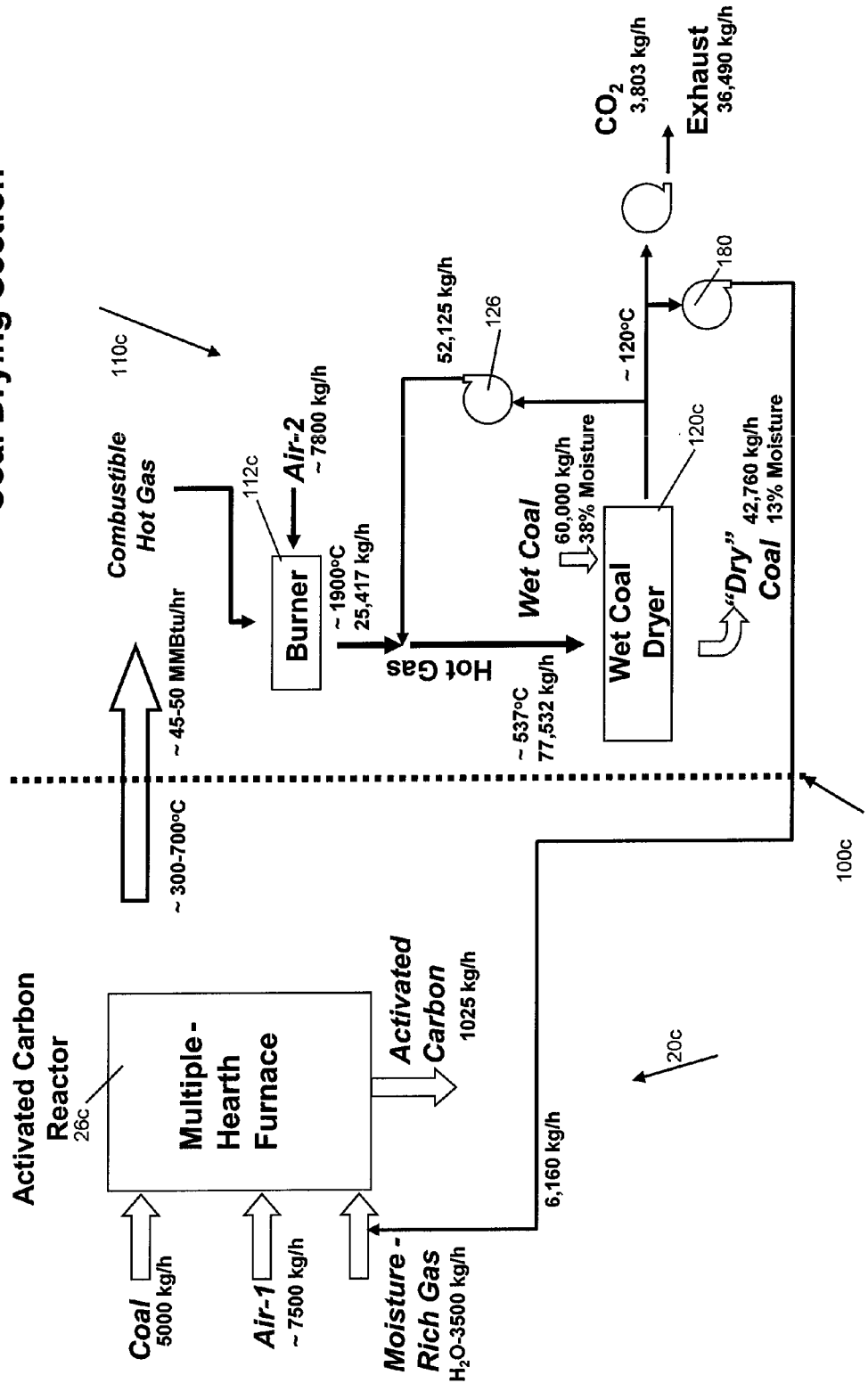
FIG. 11 is a schematic flow diagram of a process for the co-production of activated carbon and upgraded "dried" coal using thermal drying with high-moisture gas recycle to the activated carbon furnace according to the invention.

Coal (lignite) of the composition provided in Example 9 is used as feed stock for activated carbon. A higher moisture (38 weight % $H_2O$) coal, similar to Example 9, is used as feed stock for the coal drying section (110c) in the proposed inventive method (FIG. 11). In this method, a recycle fan (180) takes a portion of the exhaust from the dryer (120c), which has a high moisture content resulting from the evaporation of water from the wet coal in the dryer, and recycles it to the activated carbon manufacturing section (20c). The high-moisture content recycle gas is used as steam for activation of the coal in the activated carbon reactor (26c). If an indirect dryer is used, this stream would be completely composed of water vapor. If a direct fired dryer is used, the moisture content of the gases is lower, but still relatively high. The gas composition (volume percent) of the recycle stream is as shown below for a direct coal fired dryer in this example:

| | |
|---|---|
| $CO_2$ | 5.3% |
| $H_2O$ | 68.2% |
| $O_2$ | 1.2% |
| $N_2$ | 25.3% |

Since the water vapor for the production of activated carbon is obtained from the recycle gas and separate steam does not have to be generated in the burner/combustor/boiler section (112c) in this example, all of the chemical and thermal energy in the hydrogen-rich syngas from the activated carbon production reactor can be used for drying in the coal dryer (120c). Consequently a larger quantity of moisture can be evaporated in the coal dryer (120c) compared to the dryer (120a) in Example 9. In this case, the wet coal feed rate to the dryer is 60,000 kg/hour and dry coal product rate is 42,760 kg/hour. This is higher than the product rate from the dryer (120a) in Example 9, which is 36,345 kg/hour. The corresponding $CO_2$ emissions and energy efficiency are identical to Example 9 and are dramatically improved in relation to comparative examples (12, 13 and 14) described below.

COMPARATIVE EXAMPLES

Example 12

Separate Coal-Fired Boiler for Coal Drying

A typical coal-fired system necessary for providing the energy for coal drying as in the integrated example is estimated to require 3,050 kg/hour of coal firing. The coal considered in this case is a lignite coal as described in the example with the integrated plant. Combustion of the above indicated quantity of coal will generate about 17,710 kg/hour of flue gas, if the excess air used is about 20 percent above the stoichiometric requirement. Corresponding quantity of $CO_2$ emissions in the flue gas is about 3,867 kg/hour, which is higher than the $CO_2$ emissions (3803 kg/hour) obtained from firing the hydrogen-rich syngas from the activated carbon reactor. Additionally, no activated carbon product is produced in this example in contrast to Examples 9, and 11

Example 13

Coal-Fired Activated Carbon Plant with Flue Gas Quench

An example of a typical coal-fired activated carbon production plant is provided below. Lignite of the composition provided in the previous example is used as feed stock. Activated carbon yield is about 20 percent based on wet feed input. A portion of the heat generated from the combustion of the product gases from the reactor is used to generate process steam. Steam requirement for the activated carbon production plant is about 0.7 kg of steam per kilogram of wet feed. For a 5,000 kg/hour wet lignite input, this translates to about 3,500 kg/hour of steam. This plant yields about 1,025 kg/hour of activated carbon product. The remainder of the heat from the combustion of the product gas from the activated carbon production reactor has to be quenched with a water spray. About 14,285 kg/hour of water is required to quench the flue gases and achieve an outlet flue gas temperature of about 300° F., which is optimum for operation of the pollution control equipment. This process yields a $CO_2$ emission of about 3,803 lb/hour, but the energy in the hydrogen-rich combustible gases is not utilized. No additional dry coal co-product is generated in this example in contrast to Examples 9, 10 and 11.

Example 14

Coal-Fired Activated Carbon Plant with Heat Recovery for Power Generation

In a typical coal-fired activated carbon production plant flow diagram with heat recovery for power generation, lignite of the composition provided in the previous examples is used as feed stock. Activated carbon yield is about 20 percent based on wet feed input. A portion of the heat generated from the combustion of the product gases from the reactor is used to generate process steam. Steam requirement for the activated carbon production plant is about 0.7 kg of steam per kilogram of wet feed. For a 5,000 kg/hour wet lignite input, this translates to about 3,500 kg/hour of steam. This plant yields about 1,025 lb/hour of activated carbon product. The remainder of the heat from the combustion of the product gas from the activated carbon production reactor is cooled, while additional steam is generated. This steam is sent to a steam turbine for electricity production. About 2.5 MWe of electricity can be expected to be produced, with a heat-to-electricity conversion of about 20-25%. This process yields an overall $CO_2$ emission of about 3,803 kg/hour.

Electricity generation using a steam turbine by itself, typically only has energy efficiency utilization between 20 and 35 percent, but for a plant of this size closer to 20 percent. The remainder of the energy is lost to the environment during steam condensation in the condenser, which is necessary to return water into a liquid state before it can be compressed and returned to the boiler. No additional dry coal co-product is generated in this example in contrast to Examples 9, 10 and 11, and the efficiency of energy utilization of the combustible gases from the activated carbon reactor is lower than 50 percent.

With respect to the above description then, it is to be realized that the optimum relationships for the elements of the invention, to include variations in size, materials, shape, form, function and manner of operation, assembly and use, are deemed apparent to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will occur to those skilled in the art, it is not desired to limit the invention to the exact construction and operation shown and described, and accordingly, all suitable modifications and equivalents may be resorted to, falling within the scope of the invention.

What is claimed is:

1. A method comprising:
    a) providing a parent hydrocarbon-rich solid material;
    b) activating the parent material by exposing it to a hot gas stream at atmospheric pressure, the gas stream resulting from partial oxidation of the parent material using air along with additional carbon dioxide and/or steam, to produce activated carbon with a surface area of at least about 200 $m^2$/gm, and a hydrogen-rich carbon-deficient combustible gas that has a lower carbon to hydrogen ratio than the parent material;
    c) adding supplemental fuel to the combustible gas and then combusting at least some of the combustible gas to produce heat; and
    d) using at least about 70% of the energy content of the combustible gas to dry additional coal or biomass other than that used in step a).

2. The method of claim 1 further comprising:
    e) removing tars from the hot combustible gas stream before the gas stream is combusted by exposing the hot combustible gas to wet, cool, coal or biomass before the combustible gas is combusted to thereby simultaneously condense the tars and dry the coal or biomass, wherein at least a portion of coal or biomass dried in step d) is used to remove tars from the hot combustible gas.

3. The method of claim 1 further comprising using at least some of the heat to produce steam through boiling water, and then using the steam in step b).

4. The method of claim 3 wherein steam is raised before step d).

5. The method of claim 1 wherein CO2 emission per unit of heat produced in step c) of the method is less than would have been generated by combusting coal to generate the heat produced in step c) of the method.

6. The method of claim 1 wherein the coal or biomass is compacted before step d) to partially dry it.

7. The method of claim 1 further comprising collecting water vapor created in step d) and using such water vapor in step b).

8. The method of claim 1 wherein coal or biomass drying results in the emission of volatile organic compounds (VOCs), wherein the at least some of the VOCs are combusted to produce heat and used in the step of activating the parent material.

9. The method of claim 1 wherein the activated carbon has a surface area of at least about 400 $m^2$/gm.

* * * * *